US011432795B2

(12) United States Patent
Merritt

(10) Patent No.: US 11,432,795 B2
(45) Date of Patent: Sep. 6, 2022

(54) ALTERNATIVE ANATOMICAL BORDERS OF BLOOD VESSELS AND ASSOCIATED DEVICES SYSTEMS AND METHODS

(71) Applicant: VOLCANO CORPORATION, San Diego, CA (US)

(72) Inventor: Fergus Merritt, Rancho Cordova, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 599 days.

(21) Appl. No.: 16/351,175

(22) Filed: Mar. 12, 2019

(65) Prior Publication Data
US 2019/0282199 A1 Sep. 19, 2019

Related U.S. Application Data

(60) Provisional application No. 62/642,847, filed on Mar. 14, 2018.

(51) Int. Cl.
*A61B 8/08* (2006.01)
*A61B 8/12* (2006.01)
(Continued)

(52) U.S. Cl.
CPC ........... *A61B 8/085* (2013.01); *A61B 8/12* (2013.01); *G06T 7/10* (2017.01); *G16H 30/40* (2018.01);
(Continued)

(58) Field of Classification Search
CPC ......... A61B 8/0891; A61B 8/12; A61B 8/463; A61B 8/469; A61B 5/02007; A61B 8/085;
(Continued)

(56) References Cited

U.S. PATENT DOCUMENTS

| 6,200,268 B1 | 3/2001 | Vince et al. |
| 6,381,350 B1 | 4/2002 | Klingensmith et al. |
| 7,074,188 B2 | 7/2006 | Nair et al. |
| 7,175,597 B2 | 2/2007 | Vince et al. |

(Continued)

FOREIGN PATENT DOCUMENTS

| EP | 3460805 A1 | 3/2019 |
| WO | 2012147006 A1 | 11/2012 |
| WO | 2017199246 A1 | 11/2017 |

OTHER PUBLICATIONS

Bovenkamp, E.G.P. et al., "User-Agent Cooperation in Multiagent IVUS Image Segmentation" IEEE Transactions on Medical Imaging, vol. 28, No. 1, Jan. 2009.

*Primary Examiner* — Amelie R Davis

(57) ABSTRACT

The present disclosure relates generally to the imaging of blood vessels, and in particular, to the detection of one or more borders of a blood vessel. In some embodiments, a medical imaging system is configured to detect a primary border of a blood vessel and one or more alternative borders of the blood vessel. For example, in some embodiments, a medical imaging system includes an imaging device configured to obtain an image of a blood vessel, a processing unit, and a user display. The processing unit can be configured to receive the image of the blood vessel and perform an analysis of the image to identify a primary candidate border and an alternative candidate border of the blood vessel. The primary candidate border and alternative candidate border can represent candidates for a single boundary of the blood vessel.

12 Claims, 10 Drawing Sheets

(51) Int. Cl.
  *A61B 5/02*    (2006.01)
  *A61B 5/00*    (2006.01)
  *A61B 8/00*    (2006.01)
  *G06T 7/10*    (2017.01)
  *G16H 30/40*   (2018.01)
  *G06T 7/00*    (2017.01)

(52) U.S. Cl.
  CPC ......... *A61B 5/0033* (2013.01); *A61B 5/02007* (2013.01); *A61B 8/0891* (2013.01); *A61B 8/463* (2013.01); *A61B 8/469* (2013.01); *G06T 7/0012* (2013.01); *G06T 2200/24* (2013.01); *G06T 2207/10072* (2013.01); *G06T 2207/10116* (2013.01); *G06T 2207/10132* (2013.01); *G06T 2207/20092* (2013.01); *G06T 2207/20101* (2013.01); *G06T 2207/30021* (2013.01); *G06T 2207/30101* (2013.01)

(58) Field of Classification Search
  CPC ....... G06T 2200/24; G06T 2207/10132; G06T 2207/20092; G06T 2207/30101; G06T 7/0012; G06T 7/10
  See application file for complete search history.

(56) References Cited

U.S. PATENT DOCUMENTS

| | | |
|---|---|---|
| 7,215,802 B2 | 5/2007 | Klingensmith et al. |
| 7,359,554 B2 | 4/2008 | Klingensmith et al. |
| 7,463,759 B2 | 12/2008 | Klingensmith et al. |
| 2014/0050304 A1 | 2/2014 | Florent |
| 2019/0095738 A1* | 3/2019 | Sharma .................... G06K 9/34 |

* cited by examiner

ALTERNATIVE ANATOMICAL BORDERS OF BLOOD VESSELS AND ASSOCIATED DEVICES SYSTEMS AND METHODS

TECHNICAL FIELD

The present disclosure relates generally to medical imaging systems and methods for detecting borders or anatomical features in medical images of a patient. For example, a medical imaging system can be configured to identify alternative borders, boundaries, or paths associated with the same anatomical feature of one or more blood vessels of the patient.

BACKGROUND

Physicians employ a variety of medical imaging tools to observe and assess anatomies of a patient, such as the patient's vasculature. For example, a physician may use an intravascular ultrasound (IVUS) imaging device to obtain a cross-sectional image of a blood vessel in order to investigate a potential lesion or occlusion. In other instances, a physician may use an X-ray imaging device to obtain an external view of one or more blood vessels to identify potential lesions or occlusions. An experienced physician can view the obtained images and assess the lesion or occlusion to determine whether and to what extent therapy may be required, such as the placement of a stent, application of pharmaceuticals, or surgery.

Although the obtained images can aid the physician in assessing and inspecting the vessel, the physician may also benefit from computational measurement or assessment of the vessel based on the obtained images, such as a computational identification and measurement of a circumference of the vessel. In some conventional systems, the physician must manually trace the vessel feature using a user interface device. In other conventional systems in which the boundary is identified or detected by the medical imaging system, if the physician is unsatisfied with an aspect of the identified border, the physician must manually modify the identified boundary using a user display and/or user input device.

SUMMARY

The present disclosure advantageously describes methods, systems, and devices for identifying one or more alternative borders of an anatomy or anatomical feature. For example, a medical imaging system can be configured to obtain images of one or more blood vessels and identify a plurality of alternative borders associated with the same anatomical feature (e.g., a lumen boundary, a vessel boundary, etc.). The medical imaging system can identify one border as a primary, or "best choice," border candidate. In some instances, the plurality of alternative borders can include a primary border candidate and one or more additional alternative border candidates. The borders can be identified based on an anatomical border detection algorithm. The medical imaging system can also be configured to receive a user input to select one or more of the plurality of alternative borders to be displayed to a user display, and to propagate a criterion associated with the selected border to a plurality of images of the anatomy. Such a configuration may advantageously improve a physician's workflow of identifying a correct border for an anatomical feature, such as a lumen border or a blood vessel border, because the physician can be presented with multiple options for a border, and select one or more of the plurality of alternative borders according to the physician's expertise in identifying and detecting anatomical features in a medical image. Additionally, as the medical imaging system can be configured to propagate a criterion associated with the selected border to a plurality of images, the physician need not select and/or modify identified borders in each of the plurality of images.

In some aspects of the present disclosure, a method for blood vessel border identification can include obtaining an image of a blood vessel with a medical imaging device positioned with respect to a body of a patient to obtain the image of the blood vessel, and performing, at a processing unit in communication with the medical imaging device, an analysis of the image to identify a primary candidate border and an alternative candidate border of the blood vessel. The primary candidate border and the alternative candidate border can represent candidates for a single boundary of the blood vessel. Further, the method can include outputting, to a user display in communication with the processing unit, the image of the blood vessel and the primary candidate border overlaid on the image of the blood vessel.

In some embodiments, the method can further include receiving, at a user interface in communication with the processing unit, an input from a user to either proceed with the primary candidate border, or to reject the primary candidate border and output to the user display the alternative candidate border overlaid on the image of the blood vessel. The method can further include receiving, at the user interface and in response to the input rejecting the primary candidate border, an input from the user to accept the alternative candidate border. In some embodiments, the obtaining the image of the blood vessel includes obtaining the image of the blood vessel using a medical imaging device positioned inside the body of the patient. The medical imaging device can include an intravascular imaging catheter. The primary candidate border and the alternative candidate border can represent candidates for a single circumference of the blood vessel.

In other embodiments, the obtaining the image of the blood vessel can include obtaining the image of the blood vessel using a medical imaging device positioned outside the body of the patient. In that regard, the medical imaging device can include at least one of an X-ray imaging device, an MRI imaging device, an external ultrasound device, or a computed tomography (CT) device. In some embodiments, the primary candidate border and alternative candidate border can represent different blood vessels. The method can further include receiving, at a user interface in communication with the processing unit, an input from a user to either proceed with the primary candidate border, or to reject the primary candidate border and output to the user display the alternative candidate border overlaid on the image of the blood vessel. The performing the analysis to identify the primary candidate border and the alternative candidate border can include performing a blood vessel segmentation analysis. In that regard, the receiving the input can include receiving a blood vessel location input identifying a location on the image of the blood vessel. The performing the blood vessel segmentation analysis can include identifying a plurality of blood vessels in the image, comparing each of the plurality of blood vessels to the identified location on the image, and identifying a primary candidate blood vessel and an alternative candidate blood vessel of the image based on a proximity of each of the plurality of blood vessels to the identified location on the image. The identifying the primary candidate blood vessel and the alternative candidate blood vessel can comprise comparing a width in the image of each of the plurality of blood vessels. In some embodiments, the identifying the primary candidate blood vessel and the alternative candidate blood vessel includes comparing a path length in the image of each of the plurality of blood vessels.

In some embodiments, the primary candidate border is associated with a first criterion of the analysis and the alternative candidate border is associated with a second criterion of the analysis that is different from the first criterion. Further, the method can include obtaining a plurality of images associated with the blood vessel and performing, at the processing unit, an analysis of each of the plurality of images of the blood vessel. In that regard, the performing the analysis can include propagating the criterion associated with either the primary candidate border or the alternative candidate border to each of the plurality of images to identify a blood vessel border in each of the plurality of images.

In other aspects of the present disclosure, a blood vessel border identification system can include a medical imaging device configured to obtain an image of a blood vessel, a processing unit in communication with the medical imaging device, and a user display in communication with the processing unit and configured to display the image of the blood vessel with the primary candidate border overlaid on the image. The processing unit can be configured to receive the image of the blood vessel and perform an analysis of the image to identify a primary candidate border and an alternative candidate border of the blood vessel. The primary candidate border and alternative candidate border can represent candidates for a single boundary of the blood vessel. In some embodiments, the system further includes a user interface in communication with the processing unit. The user interface can be configured to receive an input from a user to either proceed with the primary candidate border, or to reject the candidate border and output to the display the alternative candidate border overlaid on the image. The medical imaging device can be structurally arranged to obtain the image of the blood vessel while positioned within a body of a patient, and the primary candidate border and the alternative candidate border can represent candidates for a single circumference of the blood vessel.

In other embodiments, the medical imaging device is at least one of an X-ray imaging device, an MRI imaging device, an external ultrasound device, or a computed tomography (CT) device, and the primary candidate border and alternative candidate border represent different blood vessels. Further, the system can include a user interface can be configured to receive a blood vessel location input identifying a location on the image of the blood vessel, and the processing unit can be configured to identify a plurality of blood vessels in the image, compare each of the plurality of blood vessels to the identified location on the image, and identify a primary candidate blood vessel and an alternative candidate blood vessel based on a proximity of each of the plurality of blood vessels to the identified location on the image.

In some embodiments, the primary candidate border is associated with a first criterion of the analysis, and the alternative candidate border is associated with a second criterion of the analysis different from the first criterion. In that regard, the medical imaging device can be configured to obtain a plurality of images associated with the blood vessel, and the processing unit can be configured to propagate the criterion associated with either the primary candidate border or the alternative candidate border to each of the plurality of images to identify a blood vessel border in each of the plurality of images.

In some aspects of the present disclosure, a method for blood vessel border identification, can include obtaining an image of a blood vessel with a medical imaging device positioned with respect to a body of a patient to obtain the image of the blood vessel, and performing, at a processing unit in communication with the medical imaging device, an analysis of the image to identify a first candidate border and a second candidate border of the blood vessel. The first candidate border and the second candidate border can comprise alternatives for a single boundary of the blood vessel. The method can further include outputting, to a user display in communication with the processing unit, the image of the blood vessel, and the first candidate border and the second candidate border overlaid on the image of the blood vessel. The method can further include receiving, at a user interface in communication with the processing unit, a border selection input from a user to select the first candidate border or the second candidate border, and outputting, to the user display, the image of the blood vessel and the selected candidate border overlaid on the image of the blood vessel.

In other aspects of the present disclosure, a blood vessel border identification system can include a medical imaging device configured to obtain an image of a blood vessel, a processing unit in communication with the medical imaging device, a user display in communication with the processing unit, and a user interface in communication with the processing unit. The processing unit can be configured to receive the image of the blood vessel and perform an analysis of the image to identify a first candidate border and a second candidate border of the blood vessel. The first candidate border and second candidate border can comprise alternatives for a single boundary of the blood vessel. The user display can be configured to display, the image of the blood vessel with the first candidate border and second candidate border overlaid on the image. The user interface can be configured to receive a border selection input from a user to select the first candidate border or the second candidate border. The user display can be further configured to display, in response to receipt of the border selection input, the image of the blood vessel and the selected candidate border overlaid on the image of the blood vessel.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
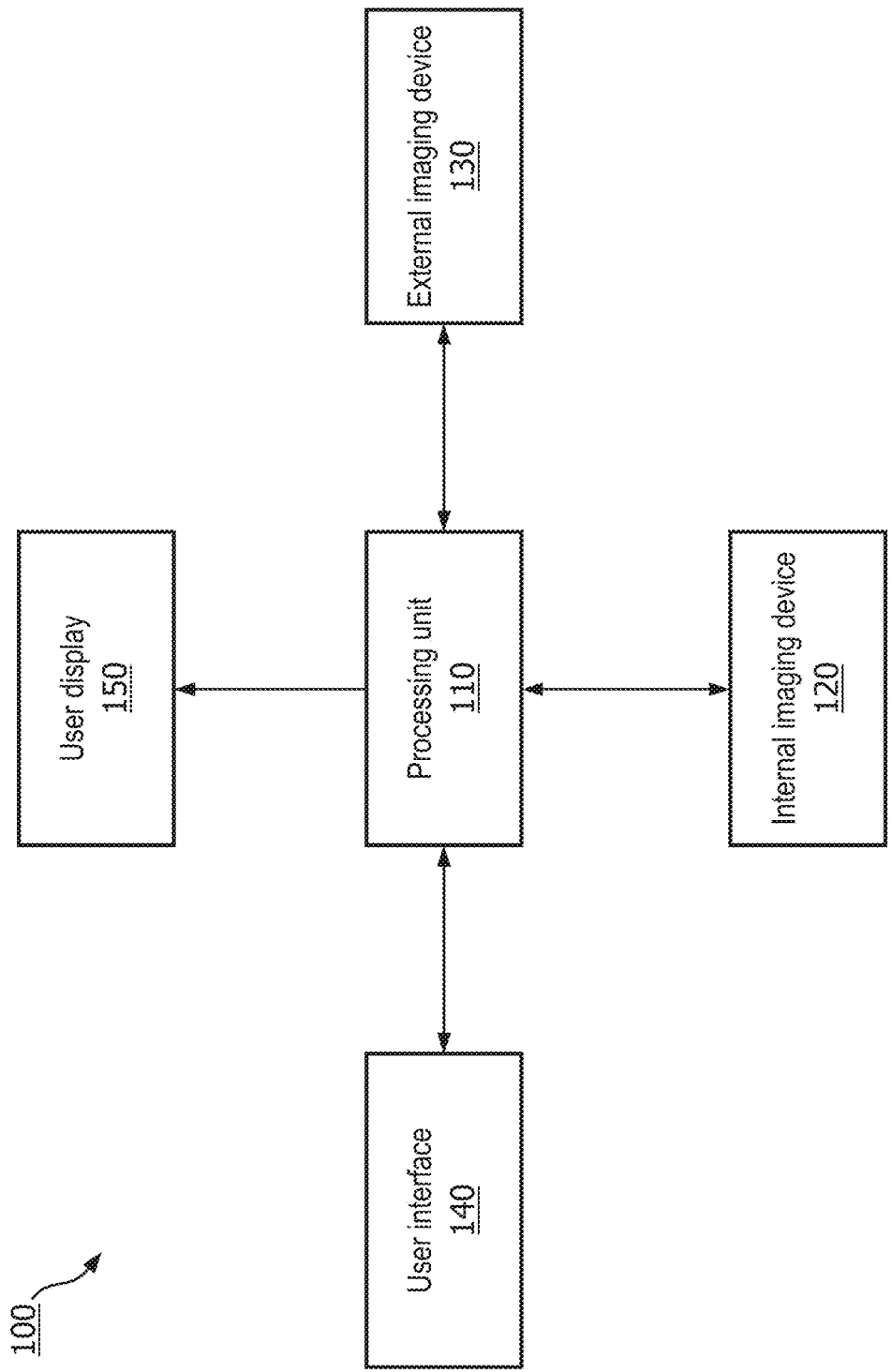
FIG. 1 is diagrammatic schematic view of a blood vessel imaging system according to some embodiments of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of a medical imaging system 100 according to some embodiments of the present disclosure. The system 100 can include a processing unit 110 in communication with an internal imaging device 120, an external imaging device 130, a user interface 140, and a user display 150. In some embodiments, the processing unit 110, internal imaging device 120, external imaging device 130, user interface 140, and/or user display 150 can be separate components, or may comprise portions of an integral device or system. In some embodiments, the medical imaging system 100 may comprise an internal imaging device 120, and may not comprise an external imaging device 130, or vice versa. In some embodiments, the user interface 140 and the user display 150 may be integrated into a single user interface, such as a touchscreen display. As described in greater detail below with respect to FIGS. 5-10, the user display 150 and the user interface 140 may comprise a graphical interface comprising images, indicators, and other features displayed on the user display 150 and operable to be manipulated by a user, such as a physician.

The processing unit 110 can be configured to receive medical imaging data from the internal imaging device 120 and/or the 130 external imaging device. In some embodiments, the medical imaging data comprises images of one or more blood vessels and/or body lumens. In some embodiments, the images of the one or more blood vessels and/or body lumens can be obtained by the internal imaging device 120, such as an intravascular ultrasound (IVUS) device, an optical coherence tomography (OCT) device, an intracardiac echocardiography (ICE) device, a transesophageal echocardiography (TEE) device, and/or any suitable internal imaging device. For example, the internal imaging device 120 can be sized and shaped, structurally arranged, and/or otherwise configured to be positioned within the body of the patient, such as within anatomy having a lumen (e.g., blood vessel, heart, esophagus, etc.) In some embodiments, images obtained by the internal imaging device 120 depict a cross-sectional view of a blood vessel at one or more locations along a length of the blood vessel and/or body lumen. In other embodiments, the images of the one or more blood vessels can be obtained by the external imaging device 130, such as an X-ray angiography device, X-ray fluoroscopy device, an magnetic resonance imaging (MRI) device, a computed tomography (CT) device, an external ultrasound device, or any suitable external imaging device. The external imaging device can obtain images of an internal anatomy while positioned outside of the body of the patient. In some embodiments, images obtained by the external imaging device 130 may depict external or elevation views of one or more blood vessels and/or other body lumen.

The processing unit 110 can be configured to process the medical imaging data obtained by the internal imaging device 120 and/or the external imaging device 130, and output the medical imaging data to the user display 150. The processing unit 110 can be configured to analyze the medical imaging data to identify or detect one or more anatomical features, such as a blood vessel. For example, the processing unit 110 may be configured to perform an analysis of an image of a blood vessel to identify or detect a lumen border, a blood vessel border, an inner wall of the blood vessel, and/or an outer wall of the blood vessel. The processing unit 110 may be configured to output to the user display 150 the image of the blood vessel and the identified feature of the blood vessel overlaid on the image. The processing unit 110 can also be in communication with the user interface 140. The user interface 140 can be configured to receive a user input from a user, such as a physician, to modify the medical imaging data displayed on the user display 150, or to control one or more aspects of the internal and/or external imaging devices 120, 130. The user interface 140 can comprise one or more of a touchscreen device, a keyboard, a joystick, a computer mouse, switches, buttons, knobs, dials, or other devices configured to receive an input from a user and transmit the input from the user to the processing unit 110 and/or other components of the system 100.

Figure 2:
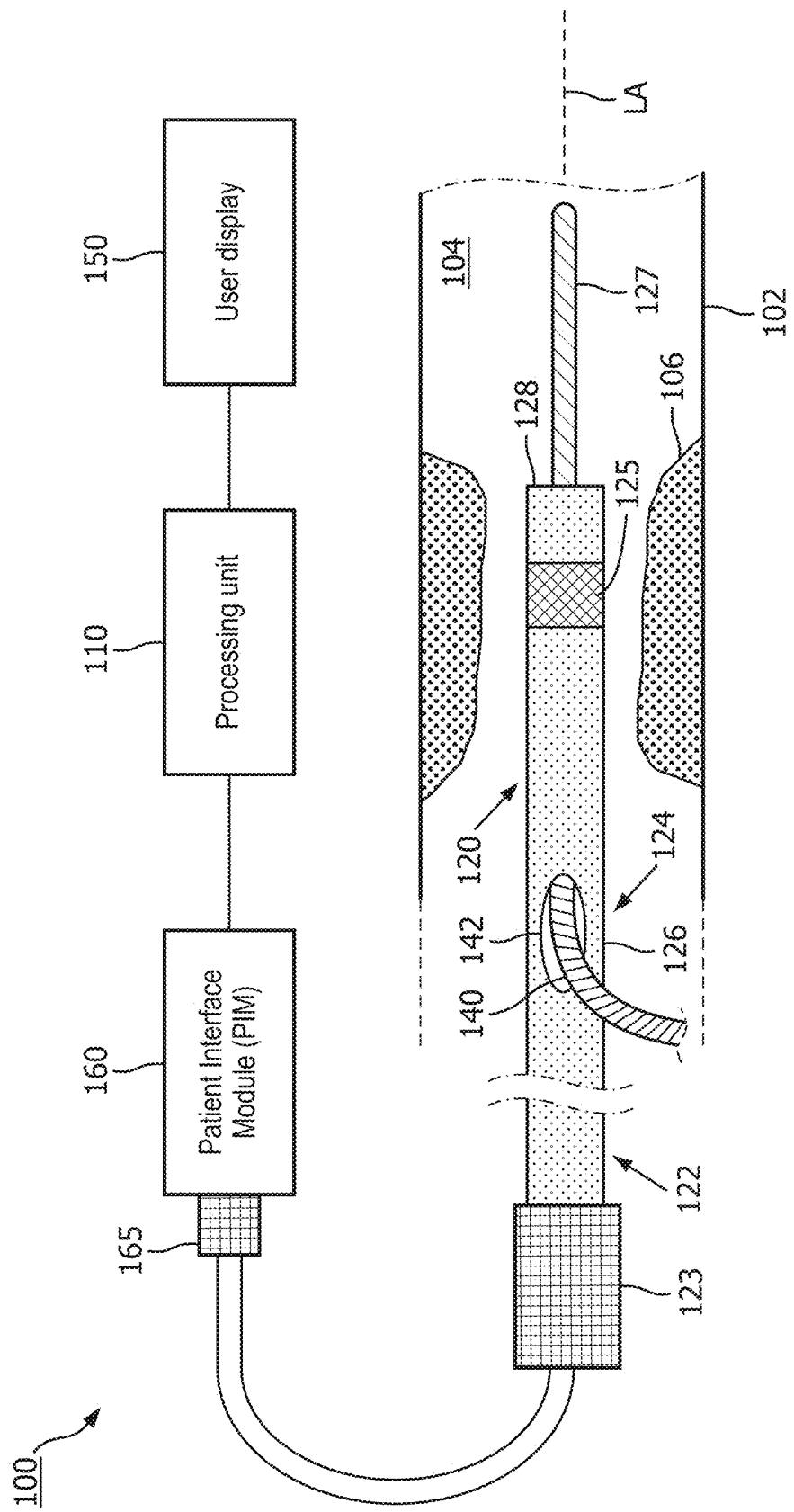
FIG. 2 is diagrammatic schematic view of a blood vessel imaging system according to some embodiments of the present disclosure.

FIG. 2 is a diagrammatic schematic view of a medical imaging system 100 according to some embodiments of the present disclosure. The system 100 includes an internal imaging device 120, such as an intravascular ultrasound (IVUS) device, a patient interface module (PIM) 160, a processing unit 110, and a user display 150. The internal imaging device 120 is structurally arranged (e.g., sized and/or shaped) to be positioned within anatomy 102 of a patient, such as a blood vessel. The internal imaging device 120 can obtain ultrasound imaging data from within the anatomy 102. The processing unit 110 can control the acquisition of ultrasound imaging data, and generates an image of the anatomy 102 (using the ultrasound imaging data received via the PIM 160) that is displayed on the user display 150.

Generally, the internal imaging device 120 can be a catheter, a guide catheter, or a guide wire. The internal imaging device 120 includes a flexible elongate member 126. As used herein, "elongate member" or "flexible elongate member" includes at least any thin, long, flexible structure structurally arranged (e.g., sized and/or shaped) to be positioned within a lumen 104 of the anatomy 102. For example, a distal portion 124 of the flexible elongate member 126 is positioned within the lumen 104, while a proximal portion 122 of the flexible elongate member 126 is positioned outside of the body of the patient. The flexible elongate member 126 can include a longitudinal axis LA. In some instances, the longitudinal axis LA can be a central longitudinal axis of the flexible elongate member 126. In some embodiments, the flexible elongate member 126 can include one or more polymer/plastic layers formed of various grades of nylon, Pebax, polymer composites, polyimides, and/or Teflon. In some embodiments, the flexible elongate member 126 can include one or more layers of braided metallic and/or polymer strands. The braided layer(s) can be tightly or loosely braided in any suitable configuration, including any suitable per in count (pic). In some embodiments, the flexible elongate member 126 can include one or more metallic and/or polymer coils. All or a portion of the flexible elongate member 126 may have any suitable geometric cross-sectional profile (e.g., circular, oval, rectangular, square, elliptical, etc.) or non-geometric cross-sectional profile. For example, the flexible elongate member 126 can have a generally cylindrical profile with a circular cross-sectional profile that defines an outer diameter of the flexible elongate member 126. For example, the outer diameter of the flexible elongate member 126 can be any suitable value for positioning within the anatomy 102, including between approximately 1 Fr and approximately 15 Fr, including values such as 3.5 Fr, 5 Fr, 7 Fr, 8.2 Fr, 9 Fr, and/or other suitable values both larger and smaller.

The internal imaging device 120 may or may not include one or more lumens extending along all or a portion of the length of the flexible elongate member 126. The lumen of the internal imaging device 120 can be structurally arranged (e.g., sized and/or shaped) to receive and/or guide one or more other diagnostic and/or therapeutic instruments. If the internal imaging device 120 includes lumen(s), the lumen(s) may be centered or offset with respect to the cross-sectional profile of the device 120. In the illustrated embodiment, the internal imaging device 120 is a catheter and includes a lumen at the distal portion 114 of the flexible elongate member 126. A guide wire 127 extends through the lumen of the device 120 between an entry/exit port 142 and an exit/entry port at a distal end 128 of the flexible elongate member 126. Generally, the guide wire 127 is a thin, long, flexible structure that is structurally arranged (e.g., sized and/or shaped) to be disposed within the lumen 104 of the anatomy 102. During a diagnostic and/or therapeutic procedure, a medical professional typically first inserts the guide wire 127 into the lumen 104 of the anatomy 102 and moves the guide wire 127 to a desired location within the anatomy 102, such as adjacent to an occlusion 106. The guide wire 127 facilitates introduction and positioning of one or more other diagnostic and/or therapeutic instruments, including the internal imaging device 120, at the desired location within the anatomy 102. For example, the internal imaging device 120 moves through the lumen 104 of the anatomy 102 along the guide wire 127. In some embodiments, the lumen of the internal imaging device 120 can extend along the entire length of the flexible elongate member 126. In the illustrated embodiment, the exit/entry port 142 is positioned proximally of the sensor 125 of the internal imaging device 120. In some embodiments, the exit/entry port 142, the exit/entry port at the distal end 128, and/or the lumen of the internal imaging device 120 is positioned distally of the sensor 125. In some embodiments, the internal imaging device 120 is not used with a guide wire, and the exit/entry port 142 can be omitted from the internal imaging device 120.

The anatomy 102 may represent any fluid-filled or surrounded structures, both natural and man-made. For example, the anatomy 102 can be within the body of a patient. Fluid can flow through the lumen 104 of the anatomy 102. In some instances, the internal imaging device 120 can be referenced as an intraluminal device. The anatomy 102 can be a vessel, such as a blood vessel, in which blood flows through the lumen 104. In some instances, the internal imaging device 120 can be referenced as an intravascular device. In various embodiments, the blood vessel is an artery or a vein of a patient's vascular system, including cardiac vasculature, peripheral vasculature, neural vasculature, renal vasculature, and/or any other suitable anatomy/lumen inside the body. The anatomy 102 can be tortuous in some instances. For example, the internal imaging device 120 may be used to examine any number of anatomical locations and tissue types, including without limitation, organs including the liver, heart, kidneys, gall bladder, pancreas, lungs, esophagus; ducts; intestines; nervous system structures including the brain, dural sac, spinal cord and peripheral nerves; the urinary tract; as well as valves within the blood, chambers or other parts of the heart, and/or other systems of the body. In addition to natural structures, the internal imaging device 120 may be used to examine man-made structures such as, but without limitation, heart valves, stents, shunts, filters and other devices.

The occlusion 106 of the anatomy 102 is generally representative of any blockage or other structural arrangement that results in a restriction to the flow of fluid through the lumen 104, for example, in a manner that is deleterious to the health of the patient. For example, the occlusion 106 narrows the lumen 104 such that the cross-sectional area of the lumen 104 and/or the available space for fluid to flow through the lumen 104 is decreased. Where the anatomy 102 is a blood vessel, the occlusion 106 may be a result of plaque buildup, including without limitation plaque components such as fibrous, fibro-lipidic (fibro fatty), necrotic core, calcified (dense calcium), blood, fresh thrombus, and/or mature thrombus. In some instances, the occlusion 106 can be referenced as thrombus, a stenosis, and/or a lesion. Generally, the composition of the occlusion 106 will depend on the type of anatomy being evaluated. Healthier portions of the anatomy 102 may have a uniform or symmetrical profile (e.g., a cylindrical profile with a circular cross-sectional profile). The occlusion 106 may not have a uniform or symmetrical profile. Accordingly, diseased portions of the anatomy 102, with the occlusion 106, will have a non-symmetric and/or otherwise irregular profile. While the anatomy 102 is illustrated in FIG. 2 as having a single occlusion 106, it is understood that the devices, systems, and methods described herein have similar application for anatomy having multiple occlusions.

The internal imaging device 120 includes an ultrasound sensor 125 at the distal portion 124 of the flexible elongate member 126. The sensor 125 is configured to emit ultrasonic energy into the anatomy 102 while the internal imaging device 120 is positioned within the lumen 104. In some embodiments, the sensor 125 includes a single ultrasound transducer. In other embodiments, the sensor 125 includes a plurality of ultrasonic transducers, such as an ultrasonic transducer array. For example, an ultrasound transducer array can include any suitable number of individual transducers between 2 transducers and 1100 transducers, including values such as 2 transducers, 4 transducers, 36 transducers, 64 transducers, 128 transducers, 500 transducers, 812 transducers, and/or other values both larger and smaller. The ultrasound transducer array can be any suitable configuration, such as phased array including a planar array, a curved array, a circumferential array, an annular array, etc. For example, the ultrasound transducer array can be a one-dimensional array or a two-dimensional array in some instances.

In some instances, the ultrasonic sensor 125 can comprise a rotational ultrasound device. The active area of the ultrasound sensor 125 can include one or more transducer materials and/or one or more segments of ultrasound elements (e.g., one or more rows, one or more columns, and/or one or more orientations) that can be uniformly or independently controlled and activated. The active area of the ultrasound sensor 125 can be patterned or structured in various basic or complex geometries. The ultrasound sensor 125 can be disposed in a side-looking orientation (e.g., ultrasonic energy emitted perpendicular and/or orthogonal to the longitudinal axis LA) and/or a forward-looking looking orientation (e.g., ultrasonic energy emitted parallel to and/or along the longitudinal axis LA). In some instances, the ultrasound sensor 125 is structurally arranged to emit and/or receive ultrasonic energy at an oblique angle relative to the longitudinal axis LA, in a proximal or distal direction. In some embodiments, ultrasonic energy emission can be electronically steered by selective triggering of one or more transducer elements of the ultrasound sensor 125.

The ultrasound transducer(s) of the sensor 125 can be a piezoelectric micromachined ultrasound transducer (PMUT), capacitive micromachined ultrasonic transducer (CMUT), single crystal, lead zirconate titanate (PZT), PZT composite, other suitable transducer type, and/or combinations thereof. Depending on the transducer material, the manufacturing process for ultrasound transducer(s) can include dicing, kerfing, grinding, sputtering, wafer technologies (e.g., SMA, sacrificial layer deposition), other suitable processes, and/or combinations thereof.

In some embodiments, the sensor 125 is configured to obtain ultrasound imaging data associated with the anatomy 102, such as the occlusion 106. The ultrasound imaging data obtained by the sensor 125 can be used by a medical professional to diagnose the patient, including evaluating the occlusion 106 of the anatomy 102. The sensor 125 can be configured to both emit ultrasonic energy into the lumen 104 and/or the anatomy 102, and to receive reflected ultrasound echoes representative of fluid and/or tissue of lumen 104 and/or the anatomy 102. As described herein, the sensor 125 can be an ultrasound imaging element, such as an ultrasound transducer and/or an ultrasound transducer array. For example, the ultrasound sensor 125 generates and emits ultrasound energy into the anatomy 102 in response to transmission of an electrical signal to the sensor 125. The ultrasound sensor 125 generates and transmits an electrical signal representative of the received reflected ultrasound echoes from the anatomy 102 (e.g., to the PIM 160 and/or processing unit 110). In various embodiments, the sensor 125 can obtain imaging data associated with intravascular ultrasound (IVUS) imaging, forward looking intravascular ultrasound (FL-IVUS) imaging, intravascular photoacoustic (IVPA) imaging, intracardiac echocardiography (ICE), transesophageal echocardiography (TEE), optical coherence tomography (OCT), and/or other suitable imaging modalities. In some embodiments, the sensor 125 and/or another sensor can obtain physiological data such as pressure, flow, temperature, fractional flow reserve (FFR), instantaneous wave-free ratio (iFR), coronary flow reserve (CFR), etc.

For diagnosis and/or imaging, the center frequency of the ultrasound sensor 125 can be between 10 MHz and 70 MHz, for example, including values such as 10 MHz, 20 MHz, 40 MHz, 45 MHz, 60 MHz, and/or other suitable values both larger and smaller. For example, lower frequencies (e.g., 10 MHz, 20 MHz) can advantageously penetrate further into the anatomy 102, such that more of the anatomy 102 is visible in the ultrasound images. Higher frequencies (e.g., 45 MHz, 60 MHz) can be better suited to generate more detailed ultrasound images of the anatomy 102 and/or fluid within the lumen 104. In some embodiments, the frequency of the ultrasound sensor 125 is tunable. For imaging, in some instances, the ultrasound sensor 125 can be tuned to receive wavelengths associated with the center frequency and/or one or more harmonics of the center frequency. In some instances, the frequency of the emitted ultrasonic energy can be modified by the voltage of the applied electrical signal and/or the application of a biasing voltage to the ultrasound sensor 125.

The ultrasound sensor 125 can include one or more electrical conductors extending along the length from the flexible elongate member 126. The electrical conductor(s) are in communication with the ultrasound sensor 125 at the distal portion 124, and an interface 123 at the proximal portion 122. The electrical conductors carry electrical signals between the processing unit 110 and the ultrasound sensor 125. For example, activation and/or control signals can be transmitted from the processing unit 110 to the ultrasound sensor 125 via the electrical conductors. Electrical signals representative of the reflected ultrasound echoes can be transmitted from the ultrasound sensor 125 to the processing unit 110 via the electrical conductors.

The internal imaging device 120 includes an interface 123 at the proximal portion 122 of the flexible elongate member 126. In some embodiments, the interface 123 can include a handle. For example, handle can include one or more actuation mechanisms to control movement of the internal imaging device 120, such as deflection of the distal portion 114. In some embodiments, the interface 123 can include a telescoping mechanism that allows for pullback of the internal imaging device 120 through the lumen. In some embodiments, the interface 123 can include a rotation mechanism to rotate one or more components of the internal imaging device 120 (e.g., the flexible elongate member 126, the ultrasound sensor 125). In some embodiments, the interface 123 includes a user interface component (e.g., one or more buttons, a switch, etc.) for a medical professional to selectively activate the ultrasound sensor 125 for imaging. In other embodiments, a user interface component of the PIM 160, the processing unit 110 and/or the user display 150 allows a medical profession to selectively activate the ultrasound sensor 125 for imaging. A conduit including, e.g., electrical conductors, extends between the interface 123 and the connector 165. The connector 165 can be configured to mechanically and/or electrically couple the internal imaging device 120 to the PIM 160.

The processing unit 110, the PIM 160, and/or the intravascular device 120 (e.g., the interface 123, the ultrasound sensor 125, etc.) can include one or more controllers. The controllers can be integrated circuits, such as application specific integrated circuits (ASIC), in some embodiments. The controllers can be configured to select the particular transducer element(s) to be used for transmit and/or receive, to provide the transmit trigger signals to activate the transmitter circuitry to generate an electrical pulse to excite the selected transducer element(s), and/or to accept amplified echo signals received from the selected transducer element(s) via amplifiers of controllers. Multiple ASIC configurations with various numbers of master circuits and slave circuits can be used to create a single ultrasound wave or multi-firing ultrasound wave device.

In some embodiments, the PIM 160 performs preliminary processing of the ultrasound echo data prior to relaying the data to the processing unit 110. In examples of such embodiments, the PIM 160 performs amplification, filtering, and/or aggregating of the data. In an embodiment, the PIM 160 also supplies high- and low-voltage DC power to support operation of the device 120 including circuitry associated with the ultrasound sensor 125. The PIM 160 can be an isolation device as, in various surgical settings, patient safety requirements mandate physical and electrical isolation of the patient from one or more high voltage components. The processing unit 110 receives imaging data (e.g., electrical signals representative of the ultrasound echo data) from the ultrasound sensor 125 by way of the PIM 160. The processing unit 110 can include processing circuit, such as processor and/or memory. The processing unit 110 processes the data to reconstruct an image of the anatomy. The processing unit 110 outputs image data such that an image of the anatomy 102, such as a cross-sectional IVUS image of a vessel, is displayed on the user display 150. The processing unit 110 and/or the user display 150 can include one or more user interface elements (e.g., touchscreen, keyboard, mouse, virtual buttons on a graphical user interface, physical buttons, etc.) to allow a medical professional to control the device 120, including one or more parameters of the ultrasound sensor 125. In some embodiments, the one or more user interface elements are included in a user interface, such as the user interface of FIG. 1.

Figure 3:
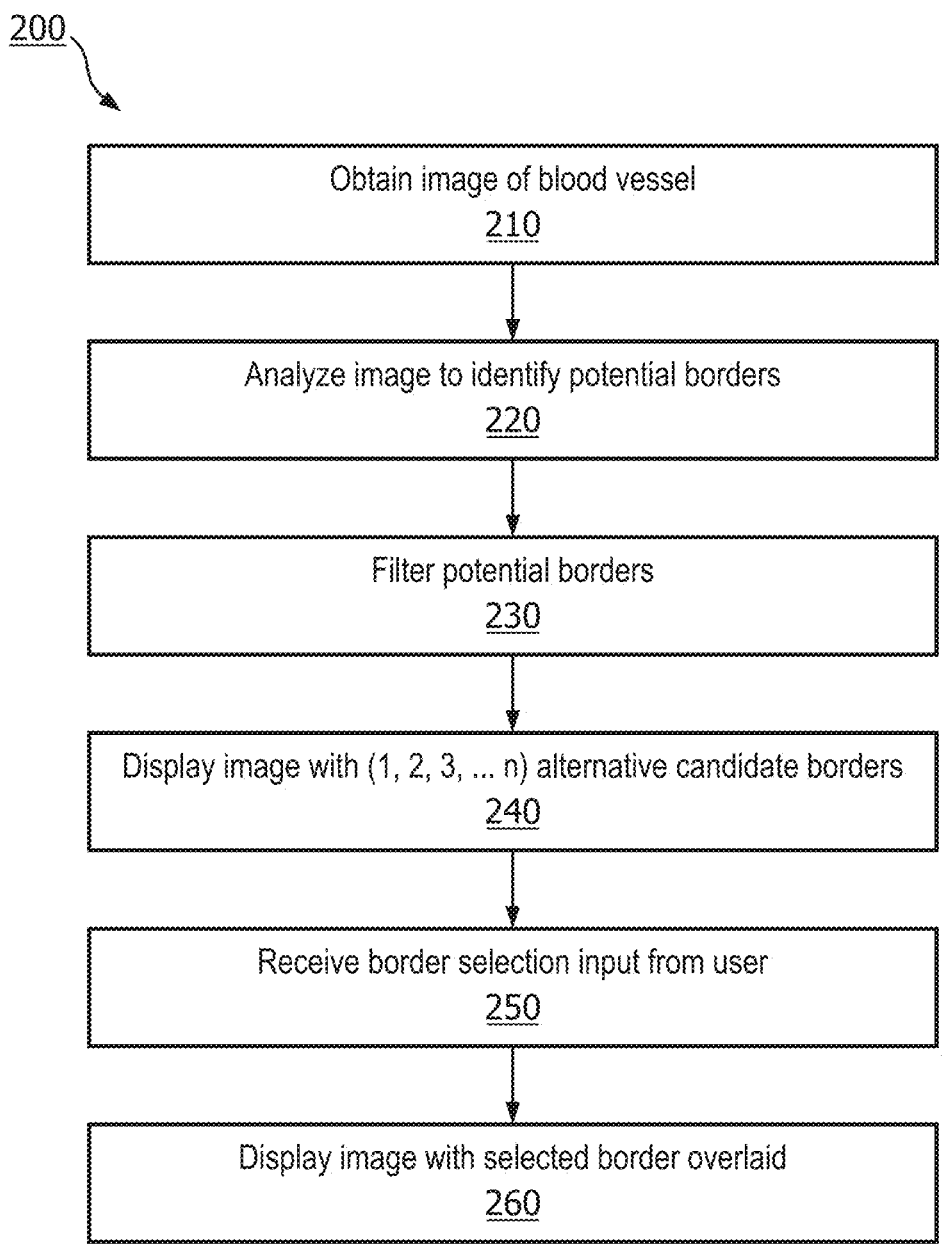
FIG. 3 is flow diagram of a method for blood vessel border identification according to some embodiments of the present disclosure.
Figure 4:
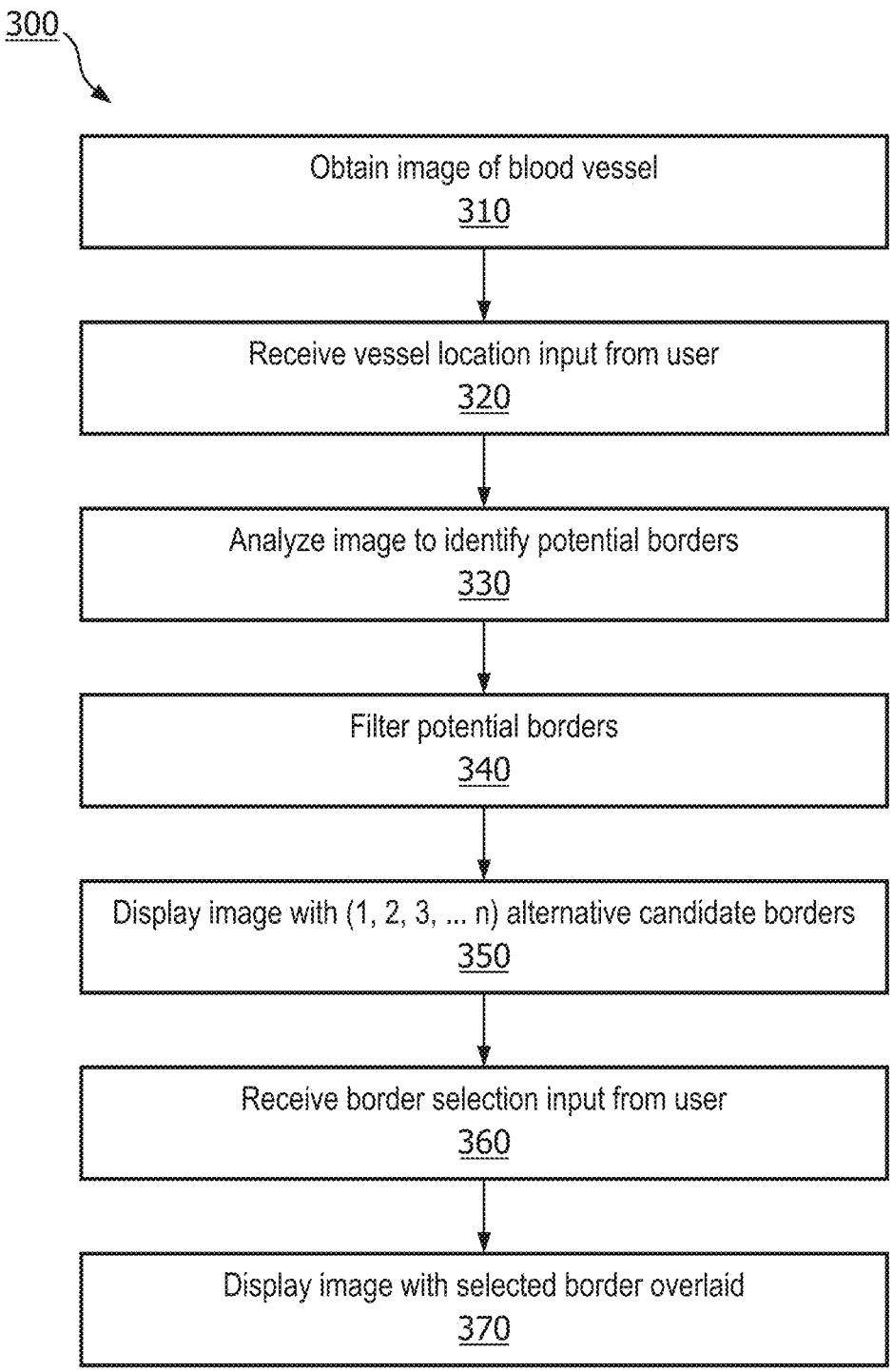
FIG. 4 is a flow diagram of a method for blood vessel border identification according to some embodiments of the present disclosure.
Figure 5:
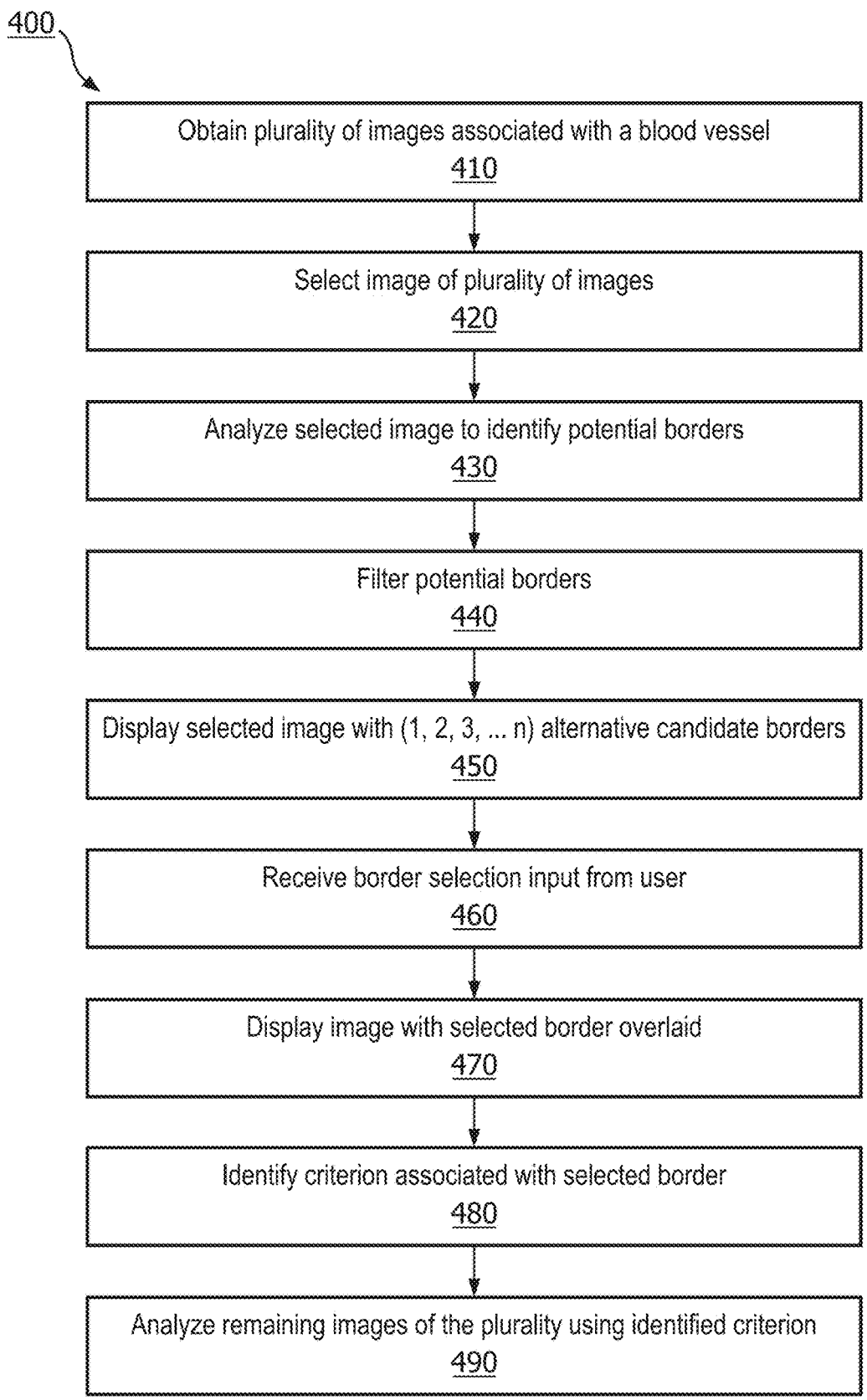
FIG. 5 is a flow diagram of a method for blood vessel border identification according to some embodiments of the present disclosure.

FIGS. 3-5 depict various methods for blood vessel identification, according to some embodiments of the present disclosure. The methods described in FIGS. 3-5 can include various advantages over conventional methods and embodiments. In some conventional embodiments, a medical imaging system can analyze an image of an anatomy to identify an anatomical feature, such as a lumen border, and display the identified anatomical feature to a user display. The system may identify the anatomical feature by applying a border identification algorithm to the image of the anatomy. In some conventional embodiments, the user or physician must first identify one or more points on the image associated with a desired border. In some conventional embodiments, if the physician is not satisfied with the border identified by the system, the physician either manually adjusts the identified border using a user interface, or manually traces a new border on the image of the anatomy. The present disclosure advantageously describes medical imaging systems and methods wherein a physician can be presented with alternative borders representing the same anatomical feature. Thus, if the physician is not satisfied with a first alternative border, the physician may select a more satisfactory second alternative border according to the expertise of the physician in identifying anatomical features in a medical image. Furthermore, embodiments of the present disclosure describe medical imaging systems and methods configured to propagate a criterion associated with a border selected by the physician to a plurality of image frames of an anatomy in order to identify a corresponding border in each of the plurality of image frames associated with the same criterion.

FIG. 3 is a flow diagram illustrating a method 200 for blood vessel identification according to some embodiments of the present disclosure. In some embodiments, one or more of the steps illustrated in FIG. 3 can be carried out by a medical imaging system, such as the medical imaging system illustrated in FIGS. 1 and 2. In block 210, a medical imaging system can obtain an image of a blood vessel. The medical imaging system can comprise one or more internal or external imaging devices, such as an IVUS device, an OCT device, an ICE device, a TEE probe, an X-ray device, MRI, CT, etc. For example, in some embodiments, the image is obtained with an IVUS imaging device, and the image depicts a cross-sectional view of the blood vessel at a location within the blood vessel. In block 220, the image is analyzed to identify one or more potential borders in the image, such as a circumference of the blood vessel in the image. In some embodiments, the identified potential borders may represent an inner circumference, such as an inner wall of the blood vessel. The identified borders may comprise alternative representations of the same anatomical feature or boundary, such as the inner wall of the blood vessel at a given point along a path of the blood vessel. The analysis may be performed by one or more components of the medical imaging system, such as a processing unit, a user display, or a medical imaging device. In block 230, the potential borders are compared to one another and/or to a threshold value, and are filtered accordingly. For example, in some embodiments, one or more gradient values of the potential borders may be compared to one another, or to a threshold gradient value. The gradient value may comprise a scalar, vector, or other suitable representation of gradient. The medical imaging system may then identify one or more alternative candidate borders from the potential borders.

In block 240, the medical imaging system outputs the image of the blood vessel to a user display. The medical imaging system also outputs to the user display the one or more alternative candidate borders overlaid on the image of the blood vessel. The borders can be identified using any suitable anatomical border detection algorithm. In some embodiments, the imaging system may select one of the alternative candidate borders as a primary or "best choice" candidate border. The primary candidate border may be selected based on an associated gradient value, for example. The system may first output the primary candidate border to the user display before showing other alternative candidate borders. In some embodiments, where multiple alternative candidate borders are identified by the system, the system may output to the user display multiple alternative candidate borders simultaneously overlaid on the image of the blood vessel (e.g., FIG. 7). In other embodiments, the medical imaging system may display the alternative candidate borders overlaid on the image of the blood vessel at different times. The different times may be separated by the receipt of a user input from a user interface. For example, FIGS. 9 and 10 which are described in greater detail below, illustrate an embodiment of a graphical interface in which alternative candidate borders are overlaid on an image of a blood vessel at different times, such that a user can accept or reject a candidate border one at a time.

In block 250, the system receives a border selection input from a user. The border selection input may be transmitted to the system via a user interface. In some embodiments, the user interface may comprise a touch screen device, a mouse, a keyboard, a joystick, and/or any other suitable component configured to receive a user input associated with an alternative candidate border. The border selection input may include an instruction to select one of the one or more alternative candidate borders. In some embodiments, the system in block 240 may display only one candidate border identified by the system as a primary or a "best choice" candidate border. The border selection input can then include an instruction to proceed with the primary or best choice candidate border identified by the system if the user is satisfied with the primary candidate border. In some embodiments, if a user is satisfied with the primary candidate border displayed, no border selection input is required. For example, the primary candidate border can be accepted by default. In that regard, the system may continue to display the primary candidate border overlaid on the image of the blood vessel, and may proceed to other steps (e.g., further image processing, calculations based on primary candidate border dimensions, etc.) In other embodiments, the system in block 240 can display the primary candidate border and one or more alternative candidate borders simultaneously on the image of the blood vessel. The border selection input may include an instruction to select one of the simultaneously displayed candidate borders. In embodiments in which the primary candidate border is accepted by default, a user can provide a border selection input such that the system outputs one or more alternative candidate borders when the user is not satisfied with the primary candidate border. A further border selection input can be provided by the user to select one of the alternative candidate borders.

In some embodiments, the border selection input may include an instruction to reject one or more of the one or more alternative candidate borders and to display a different alternative candidate border. In some embodiments, the border selection input may also include an instruction to modify one of the one or more alternative candidate borders. In block 260, after an alternative candidate border has been selected by a border selection input, the system can display the image of the blood vessel with the selected candidate border overlaid on the image.

FIG. 4 is a flow chart illustrating a method 300 for blood vessel identification according to some embodiments of the present disclosure. In some aspects, the method 300 shown in FIG. 4 may be similar or identical to the method 200 shown in FIG. 3. For example, the steps of blocks 210-260 of the method 200 of FIG. 2 may be similar or identical to the steps of blocks 310 and 330-370, respectively, of the method 300 of FIG. 3. In some embodiments, one or more of the steps of the method 300 may be carried out by a medical imaging system. In some embodiments, the medical imaging system used for the method 300 may comprise an external imaging system. In block 310, the medical imaging system can obtain an image of one or more blood vessels. For example, in some embodiments, the image is obtained with an X-ray imaging device, and the image depicts an external view of a plurality of blood vessels within a body of a patient. In block 320, the medical imaging system can receive a vessel location input from a user identifying a location on the image. In some embodiments, the identified location may indicate or represent a region of one or more blood vessels that the physician desires to inspect. In block 330, the image is analyzed to identify one or more potential borders in the image, such as borders, boundaries, or outlines of the one or more blood vessels in the image. The analysis may be performed by one or more components of the medical imaging system, such as a processing unit, a user display, or the medical imaging device. In block 340, the potential borders are compared to one another and/or to a threshold value, and are filtered accordingly. For example, in some embodiments, the locations of each of the potential borders may be compared to the identified location received in block 320 to determine whether each of the potential borders are at or near the identified location. If a potential border is not sufficiently proximal to the identified location, the potential border may be ignored or discarded.

In block 350, the medical imaging system outputs the image of the blood vessel to a user display. The medical imaging system also outputs to the user display the one or more alternative candidate borders overlaid on the image of the one or more blood vessels. The borders can be identified using any suitable anatomical border detection algorithm. The alternative candidate borders may comprise alternative representations of the same anatomical feature or boundary, such as the inner wall of the blood vessel at a given point along a path of the blood vessel. In some embodiments, the imaging system may identify a primary or best choice candidate border and output the primary candidate border to the user display before outputting the other alternative candidate borders to the user display. The primary candidate border may be identified based on an associated gradient value, for example. In some embodiments in which multiple alternative candidate borders are identified by the system, the system may output to the user display multiple alternative borders simultaneously overlaid on the image of the blood vessel. In other embodiments, the medical imaging system may display the alternative candidate borders overlaid on the image of the blood vessel at different times. The different times may be separated by the receipt of a user input from a user interface. For example, FIGS. 9 and 10 which are described in greater detail below, illustrate an embodiment of a graphical interface in which alternative candidate borders are overlaid on an image of a blood vessel at different times, such that a user can accept or reject a candidate border one at a time.

In block 360, the system receives a border selection input from a user. The border selection input may be transmitted to the system via a user interface. In some embodiments, the user interface may comprise a touch screen device, a mouse, a keyboard, a joystick, and/or any other suitable component configured to receive a user input associated with an alternative candidate border. The border selection input may include an instruction to select one of the one or more alternative candidate borders. In some embodiments, the system in block 350 may display only one candidate border identified by the system as a primary or a "best choice" candidate border. The border selection input can then include an instruction to proceed with the primary or best choice candidate border identified by the system if the user is satisfied with the primary candidate border. In some embodiments, if a user is satisfied with the primary candidate border displayed, no border selection input is required. For example, the primary candidate border can be accepted by default. In that regard, the system may continue to display the primary candidate border overlaid on the image of the blood vessel, and may proceed to other steps (e.g., further image processing, calculations based on the primary candidate border dimensions, etc.) In other embodiments, the system in block 240 can display the primary candidate border and one or more alternative candidate borders simultaneously on the image of the blood vessel. The border selection input may include an instruction to select one of the simultaneously displayed candidate borders. In embodiments in which the primary candidate border is accepted by default, a user can provide a border selection input such that the system outputs one or more alternative candidate borders when the user is not satisfied with the primary candidate border. A further border selection input can be provided by the user to select one of the alternative candidate borders.

In some embodiments, the border selection input may include an instruction to reject one or more of the one or more alternative candidate borders. In some embodiments, the border selection input may also include an instruction to modify one of the one or more alternative candidate borders. In block 370, after an alternative candidate border has been selected with a border selection input, the system can display the image of the blood vessel with the selected candidate border overlaid on the image.

FIG. 5 is a flow chart illustrating a method 400 for blood vessel identification according to some embodiments of the present disclosure. In some embodiments, one or more of the steps illustrated in FIG. 5 can be carried out by a medical imaging system, such as the medical imaging system illustrated in FIGS. 1 and 2. The method 400 illustrated in FIG. 5 may include similar steps as described in FIGS. 3 and 4. More specifically, the steps shown in blocks 430-470 may be similar or identical to the steps of the method 200 shown in blocks 220-260 of FIG. 3. In block 410, a medical imaging system obtains a plurality of images associated with a blood vessel. In some embodiments, each of the plurality of images may be obtained at different locations of the blood vessel, or at different times or orientations within the blood vessel. In some embodiments, the plurality of images may be obtained sequentially along a length of the blood vessel. In some embodiments, the plurality of images obtained along the length of the blood vessel may be used to create a two-dimensional and/or three-dimensional representation of the blood vessel. In block 420, one of the plurality of images of the blood vessel is selected. In some embodiments, the selected image may be the first or last image obtained sequentially along a length of the blood vessel, or may be an intermediate image obtained along the length of the blood vessel.

In block 430, the image is analyzed to identify one or more potential borders in the image, such as a circumference of the blood vessel in the image. In some embodiments, the identified potential borders may represent a lumen border, a blood vessel border, an inner wall of the blood vessel, and/or an outer wall of the blood vessel. The analysis may be performed by one or more components of the medical imaging system, such as a processing unit, a user display, or the medical imaging device. In block 440, the potential borders are compared to one another and/or to a threshold value, and are filtered accordingly. For example, in some embodiments, one or more gradient values of the potential borders may be compared to one another, or to a threshold gradient value. The gradient value may comprise a scalar, vector, or other suitable representation of gradient. Once filtered, the medical imaging system may identify one or more alternative candidate borders from the potential borders.

In block 450, the medical imaging system outputs the image of the blood vessel to the user display. The medical imaging system also outputs to the user display the one or more alternative candidate borders overlaid on the image of the blood vessel. The borders can be identified using any suitable anatomical border detection algorithm. In some embodiments, the system may first output a primary candidate border to the user display before outputting other alternative candidate borders. As described above, in some embodiments, the one or more alternative candidate borders may comprise alternative representations of the same anatomical feature or border, such as an inner wall of the blood vessel at a specific point along a path of the blood vessel. In some embodiments, the imaging system may select one of the alternative candidate borders as the primary candidate border. The primary candidate border may be selected based on an associated gradient value, for example. In some embodiments, where multiple alternative candidate borders are identified by the system, the system may output to the user display multiple alternative borders simultaneously overlaid on the image of the blood vessel. In other embodiments, the medical imaging system may display the alternative candidate borders overlaid on the image of the blood vessel at different times. The different times may be designated by, for example, the receipt of a user input from a user interface.

In block 460, the system receives a border selection input from a user. The border selection input may be transmitted to the system via a user interface. In some embodiments, the user interface may comprise a touch screen device, a mouse, a keyboard, a joystick, and/or any other suitable component configured to receive a user input associated with an alternative candidate border. The border selection input may include an instruction to select one of the one or more alternative candidate borders. In some embodiments, the system in block 350 may first display only the primary or a "best choice" candidate border. The border selection input can then include an instruction to proceed with the primary or best border identified by the system if the physician is satisfied with the primary candidate border. In other embodiments, if a user is satisfied with the primary candidate border displayed, no border selection input is required. For example, the primary candidate border can be accepted by default. In that regard, the system may continue to display the primary candidate border overlaid on the image of the blood vessel, and may proceed to other steps (e.g., further image processing, calculations based on the primary candidate border dimensions, etc.) In other embodiments, the system in block 240 can display the primary candidate border and one or more alternative candidate borders simultaneously on the image of the blood vessel. The border selection input may include an instruction to select one of the simultaneously displayed candidate borders. In embodiments in which the primary candidate border is accepted by default, a user can provide a border selection input such that the system outputs one or more alternative candidate borders when the user is not satisfied with the primary candidate border. A further border selection input can be provided by the user to select one of the alternative candidate borders.

In some embodiments, the border selection input may include an instruction to reject one or more of the one or more alternative candidate borders. In some embodiments, the border selection input may include an instruction to modify one of the one or more alternative candidate borders. In block 470, after an alternative candidate border has been selected with a border selection input, the system can display the image of the blood vessel with the selected candidate border overlaid on the image.

In block 480, the system may identify a criterion associated with the selected border. The criterion may comprise a gradient value, or another value associated with the selected border's position and orientation on the image. In some embodiments, the image may identify several criteria associated with the selected image. For example, the criterion, or criteria, may comprise or relate to one or more image values such as an RBG, HSV, or HSL value. In some embodiments, the criterion or criteria, may comprise coefficients of a formula used to identify contour lines in an image. In other embodiments, the criterion or criteria can comprise one or more locations on the image corresponding to an area or region on the image wherein a desired border is likely to be found. In block 490, the system can propagate the identified criterion to the remaining images of the plurality using the identified criterion to identify or detect one or more borders in each of the plurality of images. By using the identified criterion, the system may be more likely to consistently identify a border in the vessel across images. By propagating the identified criterion to each of the plurality of images, the physician may not need to revisit each of the plurality of images to ensure that a satisfactory border has been identified.

The method 400 of FIG. 5 can include a step of receiving a vessel location input from a user, as described in block 320 of the method 300 of FIG. 4. In some embodiments, a method for border identification may exclude one or more steps illustrated in FIGS. 3-5, such as the steps of filtering the potential borders as shown in blocks 230, 340, and 440. In some embodiments, a medical imaging system may analyze an image of an anatomy to determine a specific number of potential borders in the image. For example, a medical imaging system may analyze an image using 1, 2, 3, . . . , n criteria, or sets or criteria, to identify 1, 2, 3, . . . , n potential borders. In other words, in some embodiments, each of the potential borders identified by the medical imaging system can be an alternative candidate border to be displayed to a user display such that no filtering step is necessary. In some embodiments, a method may comprise selecting multiple borders from a plurality of candidate borders to be displayed to the user display. In some embodiments, a method may comprise selecting an outer border and an inner border to display both the outer border and inner border on the user display.

Figure 6:
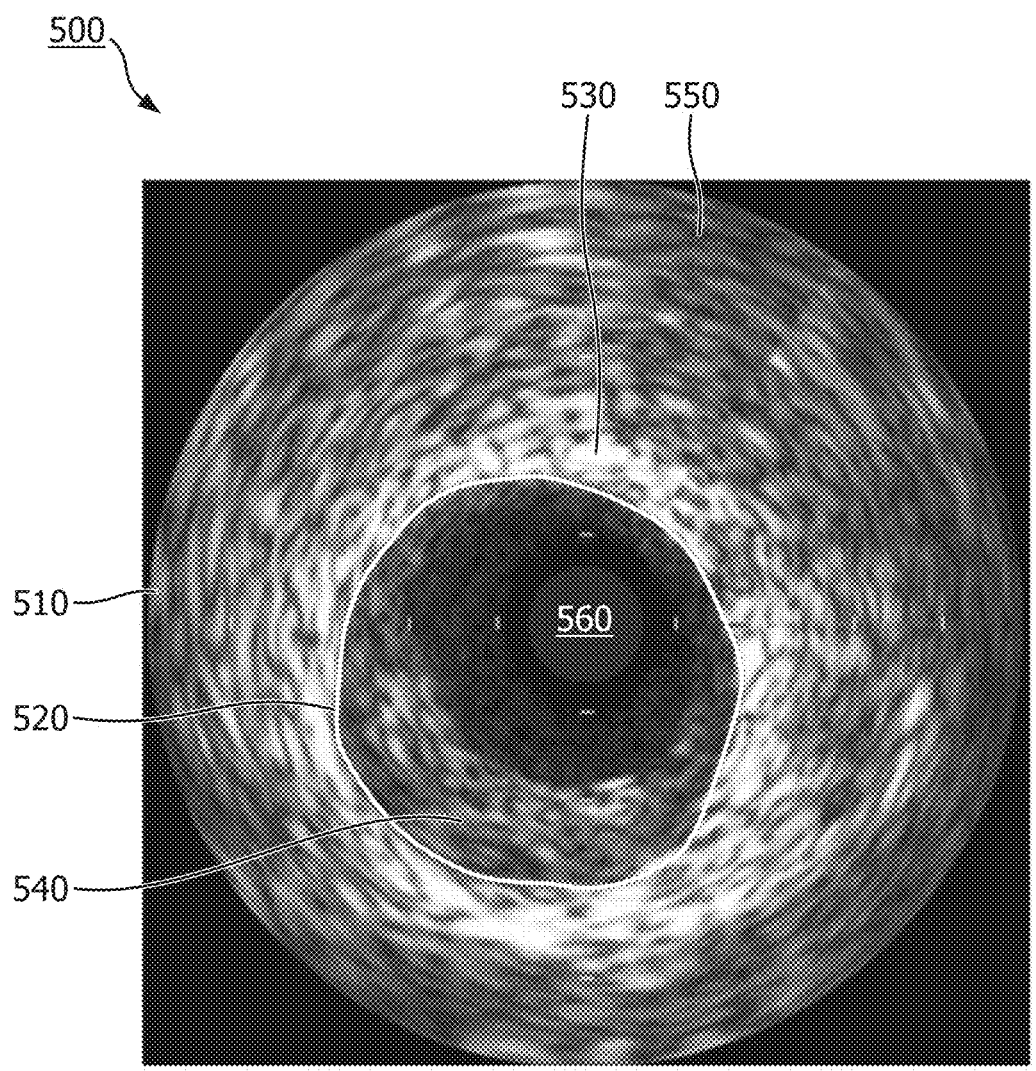
FIG. 6 is an illustration of a graphical user interface of an internal blood vessel imaging system according to some embodiments of the present disclosure.

FIG. 6 is an illustration of a graphical interface 500 of an internal imaging system, according to some embodiments. The graphical interface 500 can comprise a user display, and may be configured to receive an input from a user interface device, such as the user interface 140 shown in FIG. 1. The graphical interface 500 may include an image 510 of a blood vessel. The image 510 may comprise an IVUS image depicting a cross-section view of the blood vessel. The graphical interface 500 can comprise an identified candidate border 520 overlaid on the image 510 representing a border or boundary of the blood vessel, such as an inner wall of the blood vessel. The identified candidate border 520 may be overlaid on the image 510 at a location to representing a border or boundary of the blood vessel in the image. For example, the identified candidate border 520 may be positioned on the image 510 at or near a contour line indicating a relatively high gradient value. In other words, the identified candidate border 520 may be located between a dark area 560 and a light area 530. In the embodiment of FIG. 5, the identified candidate border 520 is located between the light area 530 and an intermediate area 540. The intermediate area 540 may represent a feature or body in the image 510 of the blood vessel, such as an occlusion or embolism. In some embodiments, the intermediate area 540 may represent plaque in the blood vessel. The intermediate area 540 may have a higher average brightness than the dark area 560, and a lower average brightness than the light area 530. The system may be configured to distinguish between the intermediate area 540 and the light area 530 to identify the candidate border 520 of the blood vessel in the image. The dark area 560 may be representative of the vessel lumen. The light area 530 may be representative of the vessel structure.

Figure 7:
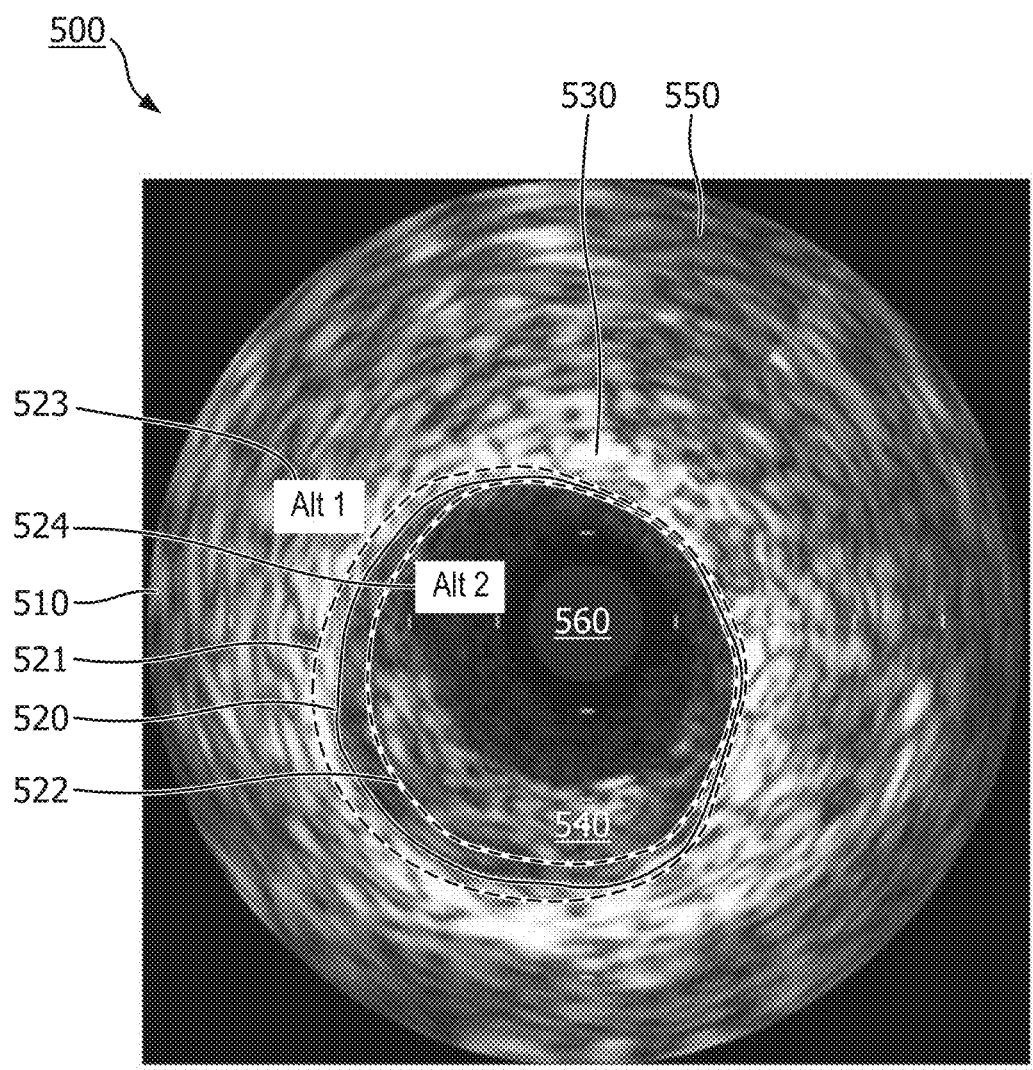
FIG. 7 is an illustration of a graphical user interface of an external blood vessel imaging system according to some embodiments of the present disclosure.

FIG. 7 is an illustration of the graphical interface 500 shown in FIG. 6, according to some embodiments of the present disclosure. In FIG. 6, a first alternative candidate border 521 and a second alternative candidate border 522 are shown overlaid on the image 510, along with the identified candidate border 520. The first and second alternative candidate borders 521, 522 may be produced by a border identification algorithm, and may represent the same anatomical feature. The first 521 or second 522 alternative candidate borders may be a better or more correct border. The embodiments of the present disclosure advantageously show the alternative candidate borders 521, 522 to a physician, who can use her expertise to select which of the alternative candidate borders 521, 522, she thinks is the better or more correct border. As in the embodiment of FIG. 7, the alternative candidate borders 521, 522 may comprise lines, shapes, and colors to distinguish the alternative candidate borders 521, 522 from the identified candidate border 520. In the embodiment of FIG. 7, the alternative candidate borders 521, 522 comprise dashed lines, while the identified candidate border 520 comprises a solid line. The alternative candidate borders 521, 522, may be identified by labels 523 and 524, respectively. The labels 523, 524 may be color-coded to more readily identify the corresponding alternative candidate borders 521, 522. In other embodiments, the labels 523, 524 may comprise other indicia to identify the corresponding alternative candidate borders 521, 522, such as an arrow or dashed line to correspond to a dashed line of the corresponding alternative candidate borders 521, 522.

The alternative candidate borders 521, 522 may diverge in some areas and may converge in other areas. The alternative candidate borders 521, 522 may be identified using criteria different from the criteria associated with the identified candidate border. In the embodiment of FIG. 7, the first alternative candidate border 521 is positioned substantially outside, or around, the identified candidate border 520, such that the first alternative candidate border 521 is positioned further within the light area 530 nearer to an outer area 550. The second alternative candidate border 522 is shown positioned substantially within the identified candidate border 520, such that all or part of the second alternative candidate border 522 is positioned within the intermediate area 540 and near the dark area 560.

In some embodiments, a medical imaging system may measure or calculate an aspect of the blood vessel, such as a cross-sectional lumen area, a circumference, a diameter, and/or a length of the blood vessel using a selected border of the image. The measured or calculated aspect of the blood vessel may aid the physician to determine whether and to what extent therapy is required in the blood vessel. For example, if the calculated lumen area of the blood vessel is below a threshold value, the physician may determine that one or more therapies are required, such as placing a stent in the blood vessel, applying pharmaceuticals, or performing a thrombectomy.

Figure 8:
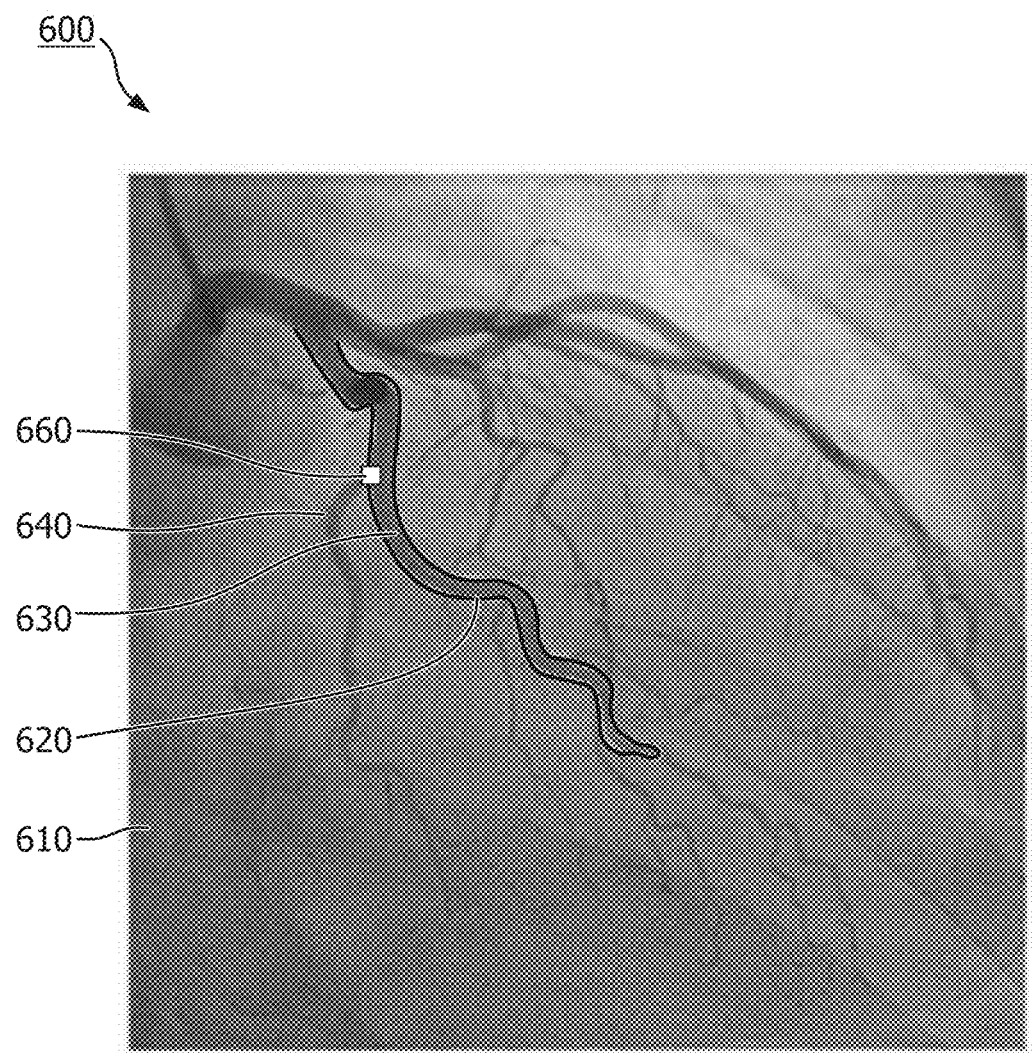
FIG. 8 is an illustration of a graphical user interface of an external blood vessel imaging system according to some embodiments of the present disclosure.

FIG. 8 is an illustration of a graphical interface 600 of an external medical imaging system, according to some embodiments of the present disclosure. The graphical interface 600 can comprise a user display, and can be configured to receive an input from a user input device, such as the user interface 140 shown in FIG. 1. The graphical interface 600 includes an image 610 of one or more blood vessels, including a first blood vessel 630, and a second blood vessel 640. The image 610 may comprise an X-ray image depicting an external view of the one or more blood vessels. The graphical interface 600 of FIG. 7 comprises a first candidate vessel 620 overlaid on the image 610 representing a border or boundary of the first blood vessel 630, such as an exterior wall or lining of the first blood vessel 630. The first candidate vessel 620 may be placed at a location on the image to indicate a boundary of the first blood vessel 630 in the image. For example, the first candidate vessel 620 may be positioned on the image 610 at or near a contour line indicating a relatively high gradient value in the image around a periphery of the first blood vessel 630. In the embodiment of FIG. 8, the first candidate vessel 620 comprises a solid line that circumscribes a portion of the first blood vessel 630. In other embodiments, the first candidate vessel 620 can comprise a shaded area overlaying the first blood vessel 630 in the image. In still other embodiments, the first candidate vessel 620 comprises a line following a path length of the first blood vessel 630.

A physician may interact with the graphical interface 600 to input a vessel location input indicating a location 660 on the image. The location 660 may be analyzed along a length of the blood vessel (e.g., a proximal portion, a distal portion). The location 660 may be an intersection between two vessels such that two different paths through different blood vessels intersect at or near the location 660. The location 660 can be the start or end point of longitudinal movement of an intraluminal device during a diagnostic or treatment procedure (e.g., an IVUS pullback). The vessel location input may be received by a processing unit and used to identify the location 660. For example, a user may view the image 610 and discover a potential occlusion or feature of the first blood vessel 630 that the physician desires to inspect. The physician may apply the vessel location input by, for example, touching a touchscreen device displaying the image 610 of the one or more blood vessel at the location 660 of the image 610. The system may identify one or more potential vessels by using the location 660 of the vessel location input.

Figure 9:
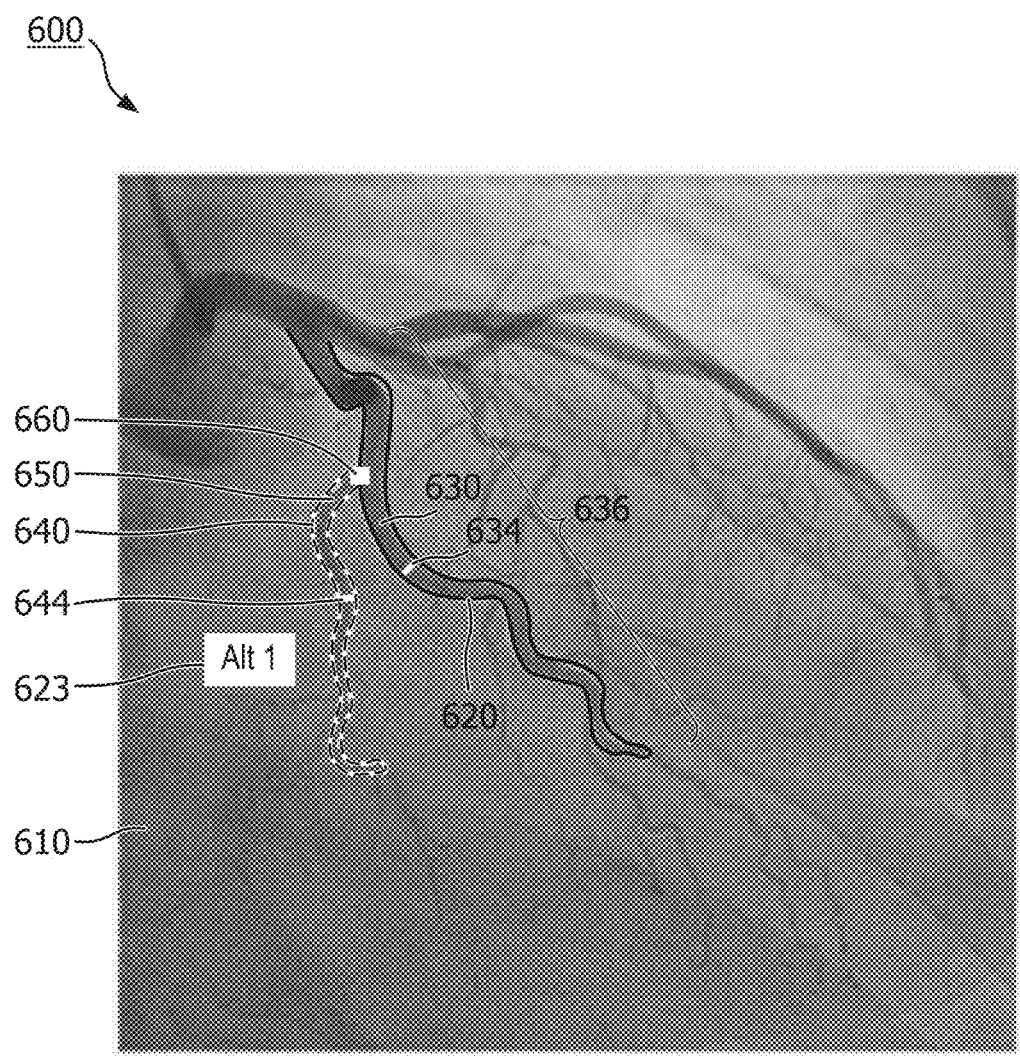
FIG. 9 is an illustration of a graphical user interface of a blood vessel imaging system according to some embodiments of the present disclosure.

FIG. 9 is an illustration of the graphical interface 600 of FIG. 8, further including a second candidate vessel 650 overlaid on the image 610. The second candidate vessel 650 may represent a border or boundary of the second blood vessel 640, such as an exterior wall or lining of the second blood vessel. FIG. 9 also shows a number of measurements 634, 644, 636 configured to characterize or describe the first and second blood vessels 630, 640. For example, the graphical interface 600 may show a first width 634 corresponding to the first blood vessel 630, and a second width 644 corresponding to the second blood vessel 640. The first and second widths 634, 644 may be obtained or measured at locations on the image proximal to the identified location 660. The first and second widths may represent a dimension of the first and second blood vessels 630, 640 in the image 610 transverse to a longitudinal axis or line path of the first and second blood vessels 630, 640 at a given location. The graphical interface 600 of FIG. 8 also depicts a length measurement of the first blood vessel. The length 636 of the first blood vessel 630 may represent a distance from a first point along the length of the first blood vessel 630 to an end point of the first blood vessel 630. Although the length 636 shown in FIG. 9 is represented by a straight line, in some embodiments, the length 636 may represent a path length of a first blood vessel 630.

In some embodiments, one or more measurements 634, 644, 636, can be used to identify one or more candidate vessels. For example, in some embodiments, a medical imaging system may identify a plurality of potential vessels in an image. The system may filter the plurality of potential vessels based on a proximity to an identified location, such as the location 660 associated with the vessel location input. In some cases, the number of potential vessels proximal to the identified location may be relatively large. Accordingly, in some embodiments, the system may compare on or more measurements of the filtered plurality of potential vessels to further filter the potential vessels to identify one or more candidate vessels. In one example, the system can compare a width, such as the first and second widths 634, 644 of each of the plurality of potential vessels. Potential vessels having a relatively small width may be ignored or discarded, while potential vessels having a relatively large width may be identified by the system as candidate vessels. In other embodiments, the system may compare a length of each of the plurality of potential vessels, such as the length 636 of the first blood vessel 630 in the image. In some embodiments, potential vessels having a relatively small length may be ignored or discarded, while potential vessels having a relatively large length may be identified as candidate vessels. In some embodiments, the system may identify 1, 2, 3, . . . , n of the potential vessels having the largest widths and/or lengths as candidate vessels to be displayed on the graphical interface 600 and analyzed.

The graphical interface 600 also comprises a label 623 or identifier for the second candidate vessel 650. As depicted in FIG. 8, the second candidate vessel 650 may be shown on the graphical interface 600 as having a profile different from that of the first candidate vessel 620. In the embodiment of FIG. 8, the alternative candidate border is shown using a dashed line. In some embodiments, the second candidate vessel 650 may be distinguished from the first candidate vessel 620 by a different color, line type, width, or a combination of distinguishing features.

Similar to the graphical interface 500 shown in FIGS. 6 and 7, the graphical interface 600 of FIG. 9 may respond to a vessel location input. For example, when the system has identified and displayed the first and second candidate vessels based on the identified location 660, the physician may select either the first candidate vessel 620 or the second candidate vessel 650 by touching, on a touchscreen display, the first or the second candidate vessel 620, 650. In other embodiments, the physician may select the first candidate vessel 620 or the second candidate vessel 650 by using a mouse to move a cursor across the graphical display to the desired candidate vessel, and clicking a mouse button to select the candidate vessel. In other embodiments, the physician may select the desired candidate vessel using a keyboard, joystick, voice command, switch, button, knob, dial, or other peripheral input device.

Although the graphical interface illustrated in FIG. 9 shows the first and second candidate vessels 620, 650 overlaid on the image 610 simultaneously, the present disclosure also contemplates embodiments in which the first and second candidate vessels 620, 650 are overlaid on the image 610 at different times. As described below with respect to the graphical interface 700 of FIGS. 10 and 11, for example, in some embodiments, a graphical interface may display a single candidate indicator overlaid on an image of an anatomy at a time, and may be configured to receive an input from a user to accept, reject, or modify the displayed candidate vessel. In some embodiments, a graphical interface may be configurable by a user to either simultaneously display multiple candidate indicators overlaid on an image, or to display a single candidate indicator overlaid on the image at a given time. In some embodiments, the candidate vessels may alternatively be referred to as candidate borders.

Figure 10:
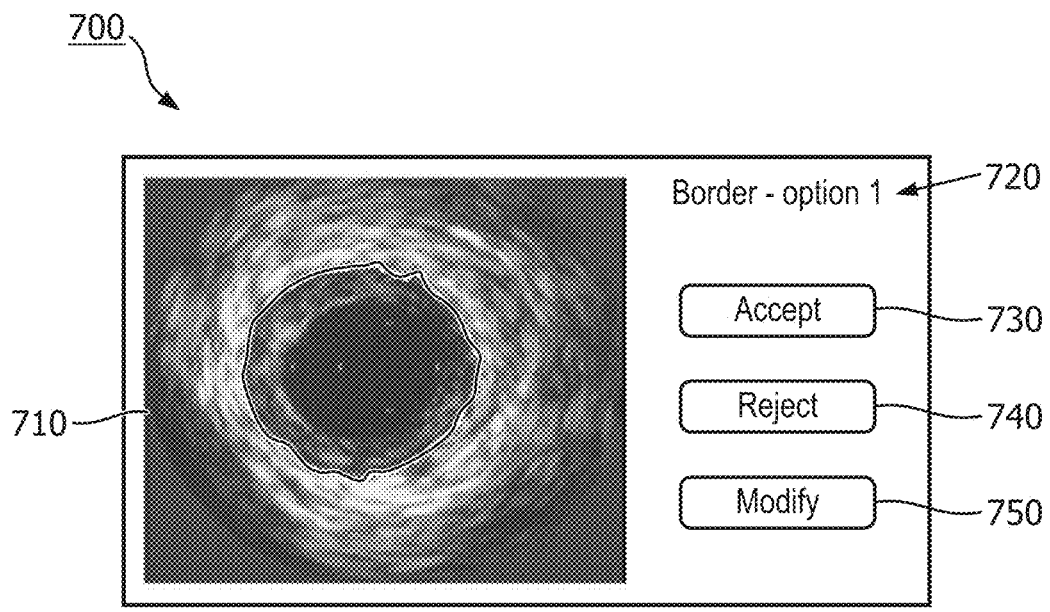
FIG. 10 is an illustration of a graphical user interface of a blood vessel imaging system according to some embodiments of the present disclosure.
Figure 11:
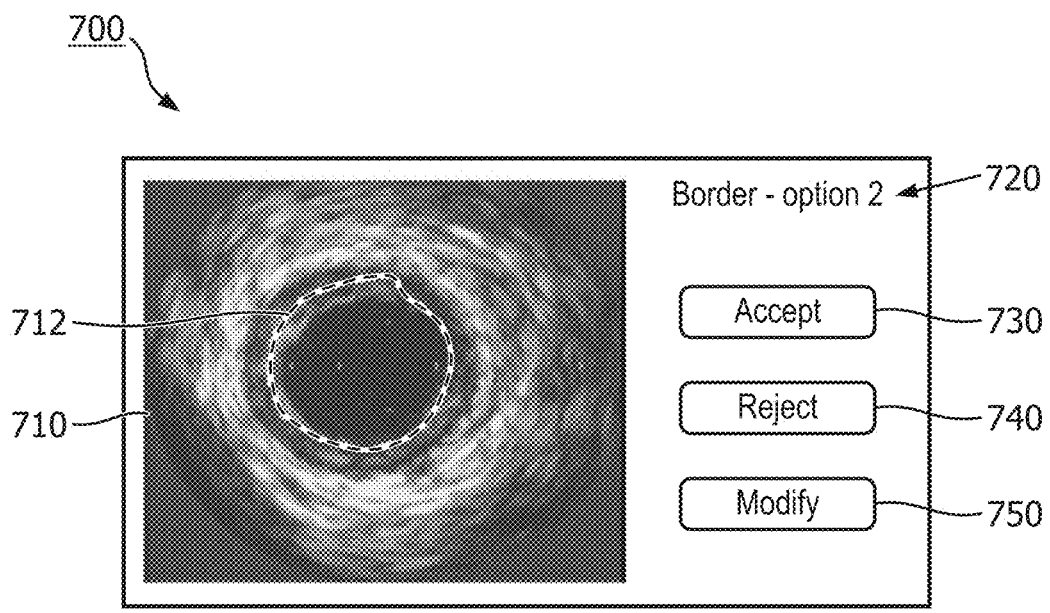
FIG. 11 is an illustration of a graphical user interface of a blood vessel imaging system according to some embodiments of the present disclosure.

FIGS. 10 and 11 are illustrations of a graphical interface 700 of an internal medical imaging system, according to some embodiments of the present disclosure. The graphical interface 700 comprises an image 710 of an anatomy, such as a blood vessel, a candidate border 711/712, a label 720, and user input selectors 730, 740, 750. The image 710 of FIGS. 10 and 11 may be obtained by an IVUS imaging device. The label 720 may correspond to the candidate border 711/712 displayed on the image 710, and may change to indicate the corresponding candidate border. For example, in FIG. 10, the label 720 shows "Border—option 1," which may correspond to a first candidate border 711 of the image 710. By contrast, in FIG. 11, the label 720 shows "Border—option 2," which may correspond to a second candidate border 712 of the image 710.

Referring to FIG. 10, the internal imaging system may display the image 710 of the blood vessel and a first candidate border 711 overlaid on the image 710. The first candidate border 711 may be identified by the internal imaging system based on a criterion. In some embodiments, the first candidate border 711 may be identified by the internal imaging system as being likely to accurately represent a border of the blood vessel in the image 710, such as an inner wall of the blood vessel. The physician may view the image 710 with the first candidate border 711 overlaid on the image 710 to determine whether the physician agrees with the placement and orientation of the first candidate border 711. If the physician agrees with the placement, shape, and orientation of the first candidate border 711, the physician may choose the "Accept" input 730 on the graphical interface 700. If the physician does not agree with the placement, shape, and orientation of the first candidate border 711, the physician may choose the "Reject" input 740 on the graphical interface 700.

Referring to FIGS. 10 and 11, if the physician chooses to reject the first candidate border 711 shown in FIG. 10, the graphical interface 700 may display the image 710 with the second candidate border 712 overlaid on the image 710. In other words, the graphical interface 700 may replace the first candidate border 711 with the second candidate border 712 in response to the physician's rejection of the first candidate border 711. The physician may again be presented with the "Accept," "Reject," and "Modify" inputs 730, 740, 750. Once again, the physician has the choice to accept, reject or modify the second candidate border 712 using the corresponding inputs 730, 740, 750. This process may be repeated for 1, 2, 3, 4, 5, n candidate borders until the physician accepts a candidate border.

In some instances, the physician may not completely agree with the placement, shape, and orientation of a candidate border, but may desire to make modifications to a candidate border instead of rejecting the candidate border altogether. In such instances, the imaging system may provide for modifications to a candidate border by receiving an input 750 from the physician instructing the system to modify one or more aspects of a candidate border, such as its shape, size, and/or position on the image 710 of the blood vessel. In some embodiments, the physician may modify a candidate border by selecting the "Modify" input 750, and by selecting a point or portion of the candidate border the physician wishes to modify, and moving the point or portion as the physician sees appropriate. To complete the modification to the candidate border, the physician may instruct the system to complete the modification by a complete modification input, such as by choosing the "Accept" input 730, or by re-selecting the "Modify" input 750 followed by the "Accept" input 730, or any other suitable input configured to complete the modification of the candidate border and proceed. In some embodiments, the modification of the candidate border by be performed using a user interface, such as the user interface described with respect to FIGS. 1 and 2.

When the physician has accepted, or modified and accepted, a candidate border, the imaging system may proceed with other imaging processing steps. For example, in some embodiments, a user obtains a plurality of images of a blood vessel. In some embodiments, each of the plurality of images may be associated with a location along a length of the blood vessel, or may be associated with a different time in which the image was obtained. In some embodiments, once the imaging system has identified a selected border of the image, the system can identify a criterion associated with the selected border, and propagate the criterion to each of the remaining images of the plurality of images to identify corresponding border in each of the plurality of images. In some embodiments, the system may create or compile a two-dimensional and/or three-dimensional representation of a length of the blood vessel by compiling and interpolating the corresponding borders in each of the plurality of images. For example, during an IVUS pullback, tens, hundreds, or thousands of image frames can be obtained. The criterion of the selected border can be propagated to all or a portion of the image frames to identify a border corresponding to the criterion of the selected border in each of the image frames. Thus, advantageously, the physician need not manually identify a border in each of the image frames.

Although the graphical interfaces depicted in FIGS. 6-7 and 10-11 depict Cartesian graphs and representations of an intravascular image, the present disclosure also contemplates other representations, such as a polar graph of the cross-sectional intravascular image, wherein the candidate borders may comprise substantially flat lines across the polar graph. As mentioned above, although the graphical interfaces shown in FIGS. 6-7 and 10-11 may comprise IVUS images, this disclosure contemplates imaging systems and graphical interfaces comprising OCT, ICE, TEE, or other anatomical and/or intraluminal images. In other embodiments, a graphical interface may comprise an external image of an anatomy, such as an external ultrasound image, X-ray angiography, X-ray fluoroscopy, or other types of images. In some embodiments, a graphical interface may comprise a plurality of different types of images, and may comprise different representations of those images. In some embodiments, a medical imaging system is configured to detect a border, boundary, or feature of other parts of a patient's anatomy, such as the esophagus, bones, organs, muscles, tendons, etc.

Detecting and characterizing anatomical features in a medical image is described in, for example, U.S. Pat. No. 6,200,268 entitled "VASCULAR PLAQUE CHARACTERIZATION" issued Mar. 13, 2001 with D. Geoffrey Vince, Barry D. Kuban and Anuja Nair as inventors, U.S. Pat. No. 6,381,350 entitled "INTRAVASCULAR ULTRASONIC ANALYSIS USING ACTIVE CONTOUR METHOD AND SYSTEM" issued Apr. 30, 2002 with Jon D. Klingensmith, D. Geoffrey Vince and Raj Shekhar as inventors, U.S. Pat. No. 7,074,188 entitled "SYSTEM AND METHOD OF CHARACTERIZING VASCULAR TISSUE" issued Jul. 11, 2006 with Anuja Nair, D. Geoffrey Vince, Jon D. Klingensmith and Barry D. Kuban as inventors, U.S. Pat. No. 7,175,597 entitled "NON-INVASIVE TISSUE CHARACTERIZATION SYSTEM AND METHOD" issued Feb. 13, 2007 with D. Geoffrey Vince, Anuja Nair and Jon D. Klingensmith as inventors, U.S. Pat. No. 7,215,802 entitled "SYSTEM AND METHOD FOR VASCULAR BORDER DETECTION" issued May 8, 2007 with Jon D. Klingensmith, Anuja Nair, Barry D. Kuban and D. Geoffrey Vince as inventors, U.S. Pat. No. 7,359,554 entitled "SYSTEM AND METHOD FOR IDENTIFYING A VASCULAR BORDER" issued Apr. 15, 2008 with Jon D. Klingensmith, D. Geoffrey Vince, Anuja Nair and Barry D. Kuban as inventors and U.S. Pat. No. 7,463,759 entitled "SYSTEM AND METHOD FOR VASCULAR BORDER DETECTION" issued Dec. 9, 2008 with Jon D. Klingensmith, Anuja Nair, Barry D. Kuban and D. Geoffrey Vince, as inventors, the teachings of which are hereby incorporated by reference herein in their entireties.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method for blood vessel border identification, comprising:
   obtaining an intravascular image of a blood vessel of a patient with an intravascular imaging catheter positioned inside the blood vessel;
   performing, at a processing unit in communication with the intravascular imaging catheter, an analysis of the intravascular image of the blood vessel to identify a plurality of candidate borders of the blood vessel, wherein the plurality of candidate borders comprises a primary candidate border and an alternative candidate border, wherein the primary candidate border and the alternative candidate border represent candidates for a single circumference of the blood vessel;
   outputting, to a user display in communication with the processing unit, a first graphical interface comprising:
      the intravascular image of the blood vessel;
      the primary candidate border overlaid on the intravascular image of the blood vessel; and
      a user input selector proximate to the intravascular image of the blood vessel;
   receiving, via a user input device in communication with the processing unit, a selection of the user input selector; and
   outputting, in response to the selection, a second graphical interface to the user display, wherein the second graphical interface comprises:
      the intravascular image of the blood vessel;
      the alternative candidate border overlaid on the intravascular image of the blood vessel; and
      the user input selector proximate to the intravascular image of the blood vessel,
   wherein the primary candidate border is visually displayed in a first manner in the first graphical interface and the alternative candidate border is visually displayed in a different, second manner in the second graphical interface.

2. The method of claim 1, wherein the selection of the user input selector in the first graphical interface corresponds to rejecting the primary candidate border.

3. The method of claim 1, further comprising receiving, via the user interface input device, a further selection of the user input selector in the second graphical interface; and
   in response to the further selection, accepting the alternative candidate border.

4. The method of claim 1, wherein the primary candidate border is associated with a first criterion of the analysis and the alternative candidate border is associated with a second criterion of the analysis that is different from the first criterion.

5. The method of claim 4, further comprising:
   obtaining a plurality of intravascular images of the blood vessel; and
   performing, at the processing unit, an analysis of each of the plurality of intravascular images of the blood vessel,
   wherein the performing the analysis comprises propagating the criterion associated with either the primary candidate border or the alternative candidate border to each of the plurality of intravascular images of the blood vessel to identify the circumference in each of the plurality of intravascular images of the blood vessel.

6. A blood vessel border identification system, comprising:
   an intravascular imaging catheter configured to obtain an intravascular image of a blood vessel of a patient while the intravascular imaging catheter is positioned inside the blood vessel;
   a processing unit configured for communication with the intravascular imaging catheter, a user input device, and a user display, wherein the processing unit is configured to:
      receive the intravascular image of the blood vessel;
      perform an analysis of the intravascular image of the blood vessel to identify a plurality of candidate borders of the blood vessel, wherein the plurality of candidate borders comprises a primary candidate border and an alternative candidate border, wherein the primary candidate border and alternative candidate border represent candidates for a single circumference of the blood vessel;
      output, to the user display, a first graphical interface comprising:
         the intravascular image of the blood vessel;
         the primary candidate border overlaid on the intravascular image of the blood vessel; and
         a user input selector proximate to the intravascular image of the blood vessel;
      receive, via the user input device, a selection of the user input selector; and
      output, in response to the selection, a second graphical interface to the user display, wherein the second graphical interface comprises:
         the intravascular image of the blood vessel;
         the alternative candidate border overlaid on the intravascular image of the blood vessel; and
         the user input selector proximate to the intravascular image of the blood vessel,
      wherein the primary candidate border is visually displayed in a first manner in the first graphical interface and the alternative candidate border is visually displayed in a different, second manner in the second graphical interface.

7. The system of claim 6, wherein the selection of the user input selector in the first graphical interface corresponds to rejecting the primary candidate border.

8. The system of claim 6, wherein the primary candidate border is associated with a first criterion of the analysis, and the alternative candidate border is associated with a second criterion of the analysis different from the first criterion.

9. The system of claim 8,
wherein the intravascular imaging catheter is configured to obtain a plurality of intravascular images of the blood vessel, and
wherein the processing unit is configured to propagate the criterion associated with either the primary candidate border or the alternative candidate border to each of the plurality of intravascular images of the blood vessel to identify the circumference in each of the plurality of intravascular images of the blood vessel.

10. The system of claim 6, wherein the primary candidate border is the only candidate border of the plurality of candidate borders displayed in the first graphical interface and the alternative candidate border is the only candidate border of the plurality of candidate borders displayed in the second graphical interface.

11. The system of claim 6, further comprising:
the user input device; and
the user display.

12. The system of claim 6, wherein the processing unit is further configured to:
receive, via the user interface input device, a further selection of the user input selector in the second graphical interface; and
in response to the further selection, accept the alternative candidate border.

* * * * *